United States Patent
Iida et al.

(10) Patent No.: US 9,766,093 B2
(45) Date of Patent: Sep. 19, 2017

(54) POSITION DETECTING SYSTEM

(71) Applicant: OLYMPUS CORPORATION, Tokyo (JP)

(72) Inventors: Takahiro Iida, Hachioji (JP); Atsushi Chiba, Hachioji (JP); Yusuke Suzuki, Hino (JP); Atsushi Kimura, Akiruno (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/381,887

(22) Filed: Dec. 16, 2016

(65) Prior Publication Data
US 2017/0108356 A1 Apr. 20, 2017

Related U.S. Application Data

(63) Continuation of application No. PCT/JP2015/081297, filed on Nov. 6, 2015.

(30) Foreign Application Priority Data

Nov. 10, 2014 (JP) ................................. 2014-228386
Mar. 30, 2015 (JP) ................................. 2015-069758

(51) Int. Cl.
*G01B 7/14* (2006.01)
*G01D 5/20* (2006.01)
(Continued)

(52) U.S. Cl.
CPC .............. *G01D 5/20* (2013.01); *A61B 1/041* (2013.01); *A61B 5/062* (2013.01)

(58) Field of Classification Search
CPC ........... A61B 1/041; A61B 5/062; A61B 1/00; G01D 5/20
(Continued)

(56) References Cited

U.S. PATENT DOCUMENTS 5,512,821 A * 4/1996 Ando ..................... G01N 27/82
324/225
2008/0172069 A1* 7/2008 Dukesherer .............. A61B 5/06
606/130
(Continued)

FOREIGN PATENT DOCUMENTS

JP 2008-79913 A 4/2008
JP 2009-226080 A 10/2009
(Continued)

OTHER PUBLICATIONS

International Search Report dated Feb. 9, 2016 received in PCT/JP2015/081297.

*Primary Examiner* — Jay Patidar
(74) *Attorney, Agent, or Firm* — Scully, Scott, Murphy & Presser, P.C.

(57) ABSTRACT

A position detecting system includes: a capsule medical device having therein a magnetic field generation coil for generating a magnetic field; detection coils configured to detect the magnetic field generated by the magnetic field generation coil, and to output detection signals; at least one reference coil configured to detect a magnetic field and to output a detection signal, and arranged at a position where a signal-to-noise ratio to the magnetic field generated by the magnetic field generation coil is smaller than a signal-to-noise ratio in each of the detection signals detected by the detection coils; and a magnetic field correction unit configured to correct magnetic field detection values based on the detection signals respectively output from the detection coils, using at least one reference magnetic field detection value that is a detection value of the magnetic field based on the detection signal output from the at least one reference coil.

15 Claims, 29 Drawing Sheets

(51) Int. Cl.
*A61B 5/06* (2006.01)
*A61B 1/04* (2006.01)

(58) Field of Classification Search
USPC ..... 324/225, 207.15; 600/117–118, 109, 160
See application file for complete search history.

(56) References Cited

U.S. PATENT DOCUMENTS

| | | |
|---|---|---|
| 2009/0093678 A1 | 4/2009 | Kimura et al. |
| 2009/0237073 A1 | 9/2009 | Uchiyama et al. |
| 2010/0060472 A1 | 3/2010 | Kimura et al. |
| 2011/0181273 A1* | 7/2011 | Iida .................... A61B 1/00158 324/207.11 |
| 2011/0258843 A1* | 10/2011 | Dukesherer .............. A61B 5/06 29/606 |
| 2012/0098523 A1 | 4/2012 | Iida |

FOREIGN PATENT DOCUMENTS

| | | |
|---|---|---|
| WO | WO 2007/123217 A1 | 11/2007 |
| WO | WO 2011/102161 A1 | 8/2011 |

\* cited by examiner

POSITION DETECTING SYSTEM

CROSS REFERENCES TO RELATED APPLICATIONS

This application is a continuation of PCT international application Ser. No. PCT/JP2015/081297, filed on Nov. 6, 2015 which designates the United States, incorporated herein by reference, and which claims the benefit of priority from Japanese Patent Application No. 2014-228386, filed on Nov. 10, 2014 and Japanese Patent Application No. 2015-069758, filed on Mar. 30, 2015, incorporated herein by reference.

BACKGROUND

1. Technical Field

The disclosure relates to a position detecting system for detecting a position of a capsule medical device introduced in a subject.

2. Related Art

Conventionally, capsule medical devices have been developed for use of acquisition of various types of information regarding an inside of a subject after introduced into the subject, or for use of administration of medicines to the subject. As an example, in the field of endoscope, a capsule endoscope configured to be introduced into a digestive organ (into a lumen) of the subject has been known. The capsule endoscope has an imaging function and a wireless communication function inside a capsule-shaped casing, and captures images while moving in the digestive organ by peristaltic movement or the like, after swallowed into the subject and sequentially and wirelessly transmits image data of images (hereinafter, also referred to as in-vivo images) inside organs of the subject. The wirelessly transmitted image data is received by a receiving device provided outside the subject and is further taken in to an image processing device such as a workstation, and predetermined image processing is applied to the image data. Accordingly, in the image processing device, the in-vivo image of the subject can be reproduced in a still image or a moving image.

In addition, systems that detect a position of a capsule medical device in a subject have been developed. For example, WO 2011/102161 discloses a position detecting system that includes a coil (hereinafter, marker coil) that generates a magnetic field, in a capsule endoscope, detects the magnetic field (hereinafter, marker magnetic field) generated by the marker coil with a magnetic field detection coil (hereinafter, sensing coil) provided outside the subject, and estimates the position of the capsule endoscope, based on strength of the detected magnetic field. In this capsule endoscope, a detection value during position detection of the capsule endoscope is corrected using a detection value of the sensing coil, which has been acquired in a state where the capsule endoscope is not positioned in a space to be detected (the marker coil is in OFF state) in advance, so that an influence of an ambient environment of the position detecting system is excluded.

SUMMARY

In some embodiments, a position detecting system includes: a capsule medical device having therein a magnetic field generation coil for generating a magnetic field; a plurality of detection coils configured to detect the magnetic field generated by the magnetic field generation coil, and to output a plurality of detection signals; at least one reference coil configured to detect a magnetic field and to output a detection signal, and arranged at a position where a signal-to-noise ratio to the magnetic field generated by the magnetic field generation coil is smaller than a signal-to-noise ratio in each of the detection signals detected by the plurality of detection coils; and a magnetic field correction unit configured to correct a plurality of magnetic field detection values based on the plurality of detection signals respectively output from the plurality of detection coils, using at least one reference magnetic field detection value that is a detection value of the magnetic field based on the detection signal output from the at least one reference coil.

In some embodiments, a position detecting system includes: a capsule medical device having therein a magnetic field generation coil for generating a magnetic field; a plurality of detection coils, each of which is configured to detect the magnetic field generated by the magnetic field generation coil, and to output a detection signal; a control unit configured to select at least one detection coil from among the plurality of detection coils; and a magnetic field correction unit configured to correct a plurality of magnetic field detection values based on a plurality of detection signals respectively output from detection coils that are not selected by the control unit from among the plurality of detection coils, using a reference magnetic field detection value that is a detection value of the magnetic field based on the detection signal output from the at least one detection coil selected by the control unit.

The above and other features, advantages and technical and industrial significance of this invention will be better understood by reading the following detailed description of presently preferred embodiments of the invention, when considered in connection with the accompanying drawings.

DETAILED DESCRIPTION

Figure 1:
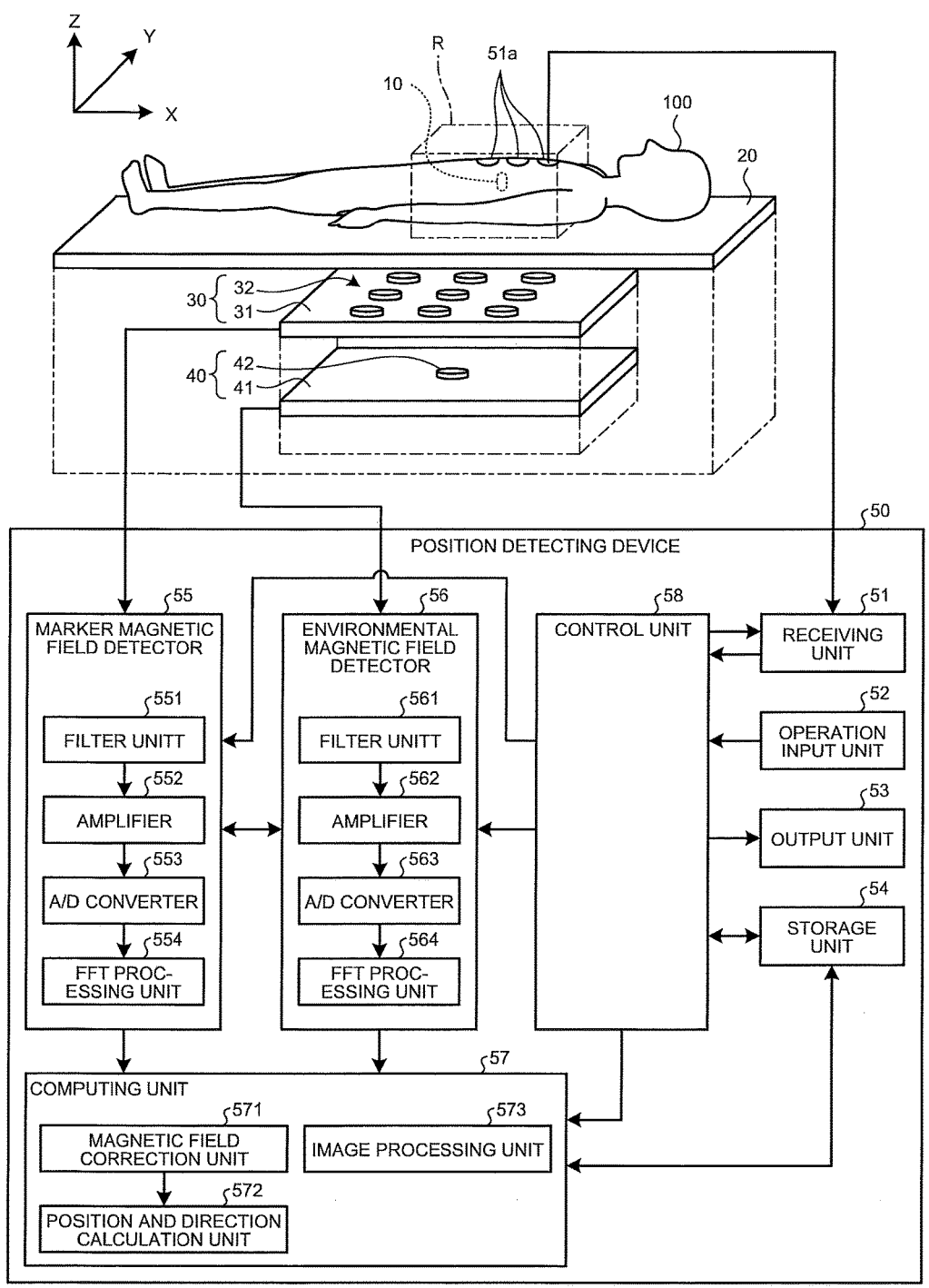
FIG. 1 is a schematic view illustrating a configuration of a position detecting system according to a first embodiment of the present invention.

Hereinafter, a position detecting system according to some embodiments of the present invention will be described with reference to the drawings. Note that, in the description below, as one form of a capsule medical device that is an object to be detected of a position detecting system according to the present embodiment, a capsule endoscope that is orally introduced into a subject and captures images of an inside of the subject (inside of a lumen) will be exemplarily described. However, the present invention is not limited by the embodiments. That is, the present invention can be applied to position detection of various capsule-shaped medical devices, such as a capsule endoscope that moves in the lumen from the esophagus to the anus of the subject, a capsule medical device that delivers medicines, or a capsule medical device including a PH sensor that measures PH in the subject.

Further, in the description below, the drawings merely schematically illustrate shapes, sizes, and positional relationship that enable understanding of content of the present invention. Therefore, the present invention is not limited only to the shapes, sizes, and positional relationship illustrated in the drawings. The same reference sings are used to designate the same elements throughout the drawings.

First Embodiment

FIG. 1 is a schematic view illustrating a configuration of a position detecting system according to a first embodiment of the present invention. As illustrated in FIG. 1, a position detecting system 1 according to the first embodiment includes a capsule endoscope 10 that superimposes image data acquired by capturing an inside of a subject 100, on a radio signal, and transmits the superimposed data, as an example of a capsule medical device introduced into a lumen of the subject 100, a sensing coil unit 30 provided under a bed 20 on which the subject 100 is placed, a reference coil unit 40 further provided under the sensing coil unit 30, and a position detecting device 50 that detects a position of the capsule endoscope 10.

Figure 2:
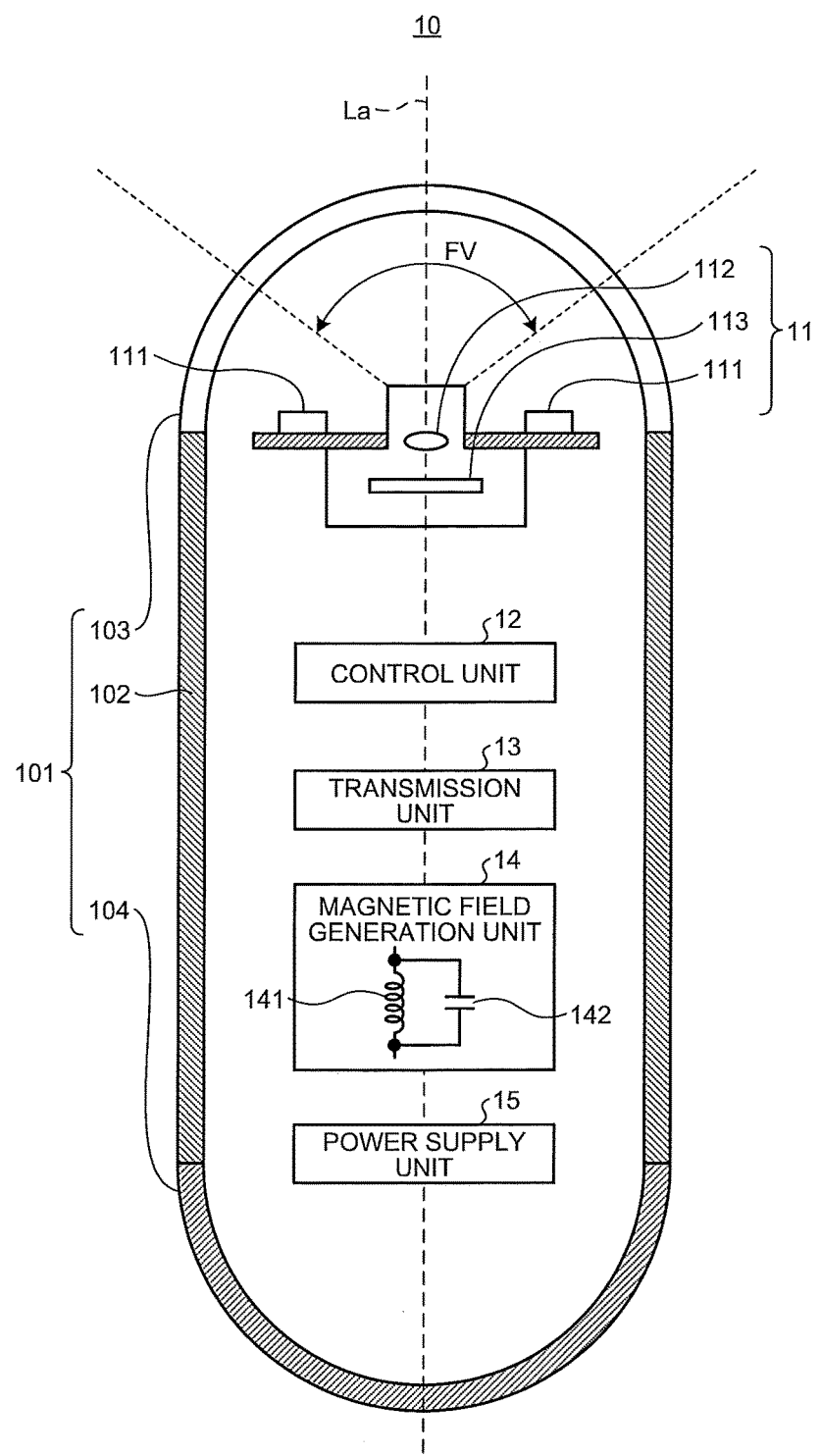
FIG. 2 is a schematic view illustrating an example of an internal structure of a capsule endoscope illustrated in FIG. 1.

FIG. 2 is a schematic view illustrating an example of an internal structure of the capsule endoscope 10 illustrated in FIG. 1. As illustrated in FIG. 2, the capsule endoscope 10 includes a capsule-shaped casing 101 small enough to be easily introduced into the lumen of the subject 100, an imaging unit 11 that is housed in the casing 101, captures the inside of the subject 100, and acquires an imaging signal, a control unit 12 that controls operations of respective units of the capsule endoscope 10 including the imaging unit 11, and applies predetermined signal processing to the imaging signal acquired by the imaging unit 11, a transmission unit 13 that wirelessly transmits the imaging signal to which the signal processing has been applied, a magnetic field generation unit 14 that generates an alternating magnetic field (hereinafter, marker magnetic field) for position detection of the capsule endoscope 10, and a power supply unit 15 that supplies power to the respective units of the capsule endoscope 10.

The casing 101 is an outer casing small enough to be introduced into organs of the subject 100, includes a cylindrical casing 102 formed into a cylindrical shape and dome-shaped casings 103 and 104 formed into a dome shape, and is configured to block both-side opening ends of the cylindrical casing 102 with the dome-shaped casings 103 and 104. The cylindrical casing 102 is formed of a colored member that is approximately semi-transparent for visible light. Further, at least one of the dome-shaped casings 103 and 104 (in FIG. 2, the dome-shaped casing 103 at the imaging unit 11 side) is formed of a transparent optical member for light in a predetermined wavelength band such as visible light. Note that, in FIG. 2, one imaging unit 11 is provided only in the dome-shaped casing 103 side. However, two imaging units 11 may be provided. In this case, the dome-shaped casing 104 is also formed of a transparent optical member. Such a casing 101 includes the imaging unit 11, the control unit 12, the transmission unit 13, the magnetic field generation unit 14, and the power supply unit 15 in a liquid-tight manner.

The imaging unit 11 is information acquisition means for acquiring the imaging signal as information on the subject 100, and includes an illumination unit 111 including a light emitting element such as an LED and a drive circuit that drives the light emitting element, an optical system 112 such as a condenser lens, and an imaging section 113 having an image sensor, such as a CMOS image sensor or a CCD, and having a drive circuit (not illustrated) that drives the image sensor. The illumination unit 111 irradiates an imaging visual field of the imaging section 113 with illumination light such as white light, and illuminates the subject 100 in the imaging visual field FV through the dome-shaped casing 103. The optical system 112 has an optical axis so as to accord with a long axis La of the casing 101, collects reflected light from the subject 100 in the imaging visual field FV, and forms an image on an imaging surface of the imaging section 113. The imaging section 113 generates the imaging signal by performing photoelectric conversion processing on an optical signal indicating an image of the subject 100 and formed on the imaging surface.

Note that, if two imaging units 11 are employed, the imaging units 11 are respectively arranged in both ends of the casing 101 at the dome-shaped casing 103 side and the dome-shaped casing 104 side such that the optical axes of the optical systems 112 accord with the long axis La of the casing 101.

The control unit 12 operates the imaging section 113 at a predetermined imaging frame rate, and causes the illumination unit 111 to emit light in synchronization with the imaging frame rate. Further, the control unit 12 applies A/D conversion and other predetermined signal processing to the imaging signal generated by the imaging unit 11 to generate image data. Further, the control unit 12 causes the magnetic field generation unit 14 to generate a magnetic field by causing the power supply unit 15 to supply the power to the magnetic field generation unit 14.

The transmission unit 13 includes a transmitting antenna (not illustrated), acquiring the image data to which the signal processing has been applied by the control unit 12 and the related information and applies modulation processing, and sequentially wirelessly transmits the image data to an outside through the transmitting antenna.

The magnetic field generation unit 14 forms a part of a resonant circuit, and includes a marker coil (first coil) 141 that generates a magnetic field as a current flows, and a capacitor 142 that forms the resonant circuit together with the marker coil 141. The magnetic field generation unit 14 generates an alternating magnetic field having a predetermined frequency as the marker magnetic field, upon receipt of the power supply from the power supply unit 15.

The power supply unit 15 is configured from a battery formed in a button shape and a switch unit such as an optical switch or a magnetic switch. In a case where the switch unit is made of a magnetic switch, the power supply unit 15 switches own ON/OFF states with a magnetic field applied from an outside, and supplies power to the respective units of the capsule endoscope 10 during an ON state. Further, the power supply unit 15 stops the power supply to the respective units of the capsule endoscope 10 during an OFF state.

Referring back to FIG. 1, the bed 20 is arranged such that a placing surface of the subject 100 becomes parallel to a horizontal plane, that is, the placing surface becomes perpendicular to a vertical direction. Hereinafter, a longitudinal direction of the bed 20 is an X direction, a short direction of the bed 20 is a Y direction, and the vertical direction (gravity direction) is a Z direction. A movable range of the capsule endoscope 10 when the subject 100 who has swallowed the capsule endoscope 10 is placed on the bed 20, that is, a typical range in which an organ to be observed exists, is set as a targeted region R, in advance.

Figure 3:
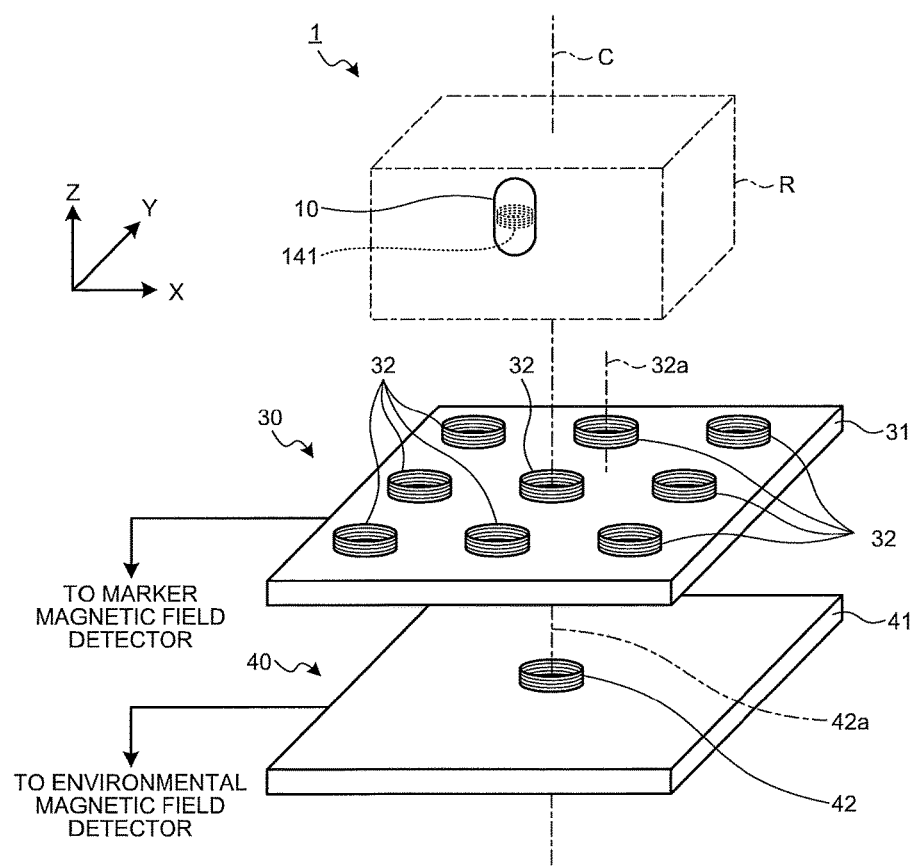
FIG. 3 is an enlarged view of a sensing coil unit and a reference coil unit illustrated in FIG. 1.

FIG. 3 is an enlarged view of the sensing coil unit 30 and the reference coil unit 40 illustrated in FIG. 1. The sensing coil unit 30 and the reference coil unit 40 are arranged to adjust centers to a central axis C of the targeted region R in the vertical direction.

The sensing coil unit 30 includes a planar panel 31 arranged in parallel to an upper surface of the bed 20, and a plurality of sensing coils (nine sensing coils in FIG. 3) (second coils) 32 arranged on a principal plane of the panel 31. Each of the sensing coils 32 is a tube-shaped coil formed in a coil spring manner having an opening diameter of about 30 to 40 mm and a height of about 5 mm, for example. Each of the sensing coils 32 receives the alternating magnetic field generated by the marker coil 141 of the capsule endoscope 10, and outputs a detection signal.

In the panel 31, the plurality of sensing coils 32 is arranged in a matrix form such that respective central axes 32a become parallel to the Z direction. Here, in the present application, the central axis of the coil is an axis that passes through an approximate center of an opening surface of the coil, and is approximately perpendicular to the opening surface. Although the arrangement of the plurality of sensing coils 32 is not especially limited. However, it is preferable to arrange the plurality of sensing coils 32 to become symmetrical (line-symmetrical or rotation-symmetrical) with respect to the central axis C of the panel 31. Accordingly, the plurality of sensing coils 32 is symmetric with respect to the central axis C of the targeted region R.

The reference coil unit 40 includes a planar panel 41 arranged in parallel to the panel 31, and a reference coil (third coil) 42 arranged on a principal plane of the panel 41. The reference coil 42 is a tube-shaped coil similar to the sensing coil 32, and detects an environmental magnetic field in an installation environment of the position detecting system 1 and outputs a reference detection signal. Hereinafter, the detection signal output by the reference coil 42 is also referred to as reference signal. The reference coil 42 is arranged to cause a central axis 42a to become parallel to the Z direction, similarly to the sensing coil 32.

The reference coil 42 is preferably arranged close to a center (on an extension of the central axis C) of the panel 41. If the reference coil 42 is arranged in the center of the panel 41, distances between the reference coil 42 and the sensing coils 32 roughly become uniform, and no sensing coils 32 are extremely close to or extremely distant from the reference coil 42. Further, the reference coil 42 becomes symmetrical with respect to the center of the targeted region R. Therefore, a situation where the capsule endoscope 10 and the reference coil 42 get too close to each other due to movement of the capsule endoscope 10 and the reference coil 42 is influenced by the marker magnetic field can be suppressed.

Next, positional relationship between the sensing coil unit 30 and the reference coil unit 40 will be described. The sensing coil unit 30 is arranged near the subject 100 during an examination so that a signal-to-noise ratio (SN ratio) to the alternating magnetic field generated by the capsule endoscope 10 becomes high. In the first embodiment, the sensing coil unit 30 is arranged under the bed 20.

In contrast, the reference coil unit 40 is arranged in a more distant position from the targeted region R than the sensing coils 32 are. Accordingly, an SN ratio in the reference signal output by the reference coil 42 to the marker magnetic field becomes smaller than the SN ratios in the detection signals output by the sensing coils 32. In the first embodiment, the reference coil unit 40 is installed on an opposite side to the targeted region R with respect to the panel 31 of the sensing coil unit 30, so that such positional relationship is realized.

It is preferable a distance between the panel 31 and the panel 41 is longer than a distance between the panel 31 and the targeted region R. This is because the strength of the magnetic field attenuates in inversely proportional to the cube of distance and thus the SN ratio in the reference coil 42 can be sufficiently made smaller than those in the sensing coils 32.

To be specific, the reference coil unit 40 is arranged such that the strength of a marker magnetic field component in the reference signal becomes a threshold Th or less. Note that if the strength is the threshold Th or less, the reference coil unit 40 is preferably arranged close to the sensing coil unit 30. This is because the marker magnetic field component in the reference signal is decreased as much as possible, and a difference between the environmental magnetic field in the position of the reference coil 42 and the environmental magnetic field in the positions of the sensing coils 32 is made as small as possible.

The threshold Th of the marker magnetic field component is determined to become a permissible error or less of a detected magnetic field of the sensing coil 32, which is required from position detection accuracy to the capsule endoscope 10. An example of a specific method of determining the threshold Th includes a method of obtaining all of the detected magnetic fields of the sensing coils 32 in a case where the marker coil 141 (capsule endoscope 10) is arranged in order in the targeted region R at given intervals, and employing a small percent of a minimum detection value as the threshold Th.

Referring back to FIG. 1, the position detecting device 50 includes a receiving unit 51 that receives the radio signal transmitted from the capsule endoscope 10 through a receiving antenna 51a, an operation input unit 52 used to input various types of information and commands to the position detecting device 50, an output unit 53 that outputs the various types of information and the like processed by the position detecting device 50 to the display device and the like, and causes the display device to display the information, a storage unit 54, a marker magnetic field detector 55 that applies various types of signal processing to the detection signals output from the sensing coils 32, an environmental magnetic field detector 56 that applies various types of signal processing to the detection signal output from the reference coil 42, a computing unit 57, and a control unit 58 that controls operations of these units.

In performing an examination by the capsule endoscope 10, a plurality of receiving antennas 51a, which receives the radio signal transmitted from the capsule endoscope 10, is attached to a body surface of the subject 100. The receiving unit 51 selects the receiving antenna 51a having the highest received strength to the radio signal, of these receiving antennas 51a, and applies demodulation processing and the like to the radio signal received through the selected receiving antenna 51a thereby to acquire the image data of the in-vivo image and the related information.

The operation input unit 52 is configured from input devices such as various buttons, a switch, and a keyboard, pointing devices such as a mouse and a touch panel, a joystick, and the like, and inputs various types of information and commands to the control unit 58 in response to input operations by a user. Examples of the information or the command input by the operation input unit 52 include information instructing start and termination of the examination with the capsule endoscope 10, and information instructing start and termination of a position detection operation to the capsule endoscope 10.

The output unit 53 includes various display devices such as a liquid crystal display and an organic EL display, and displays, on a screen, the various types of information and the commands input from the operation input unit 52, the in-vivo image of the subject 100, positional information of the capsule endoscope 10 at the time of capturing the in-vivo image, and the like.

The storage unit 54 is configured from a storage medium that stores information in a rewritable manner such as a flash memory or a hard disk, and a writing/reading device. The storage unit 54 stores various programs and parameters for controlling respective units of the position detecting device 50 by the control unit 58, the image data of the in-vivo image captured by the capsule endoscope 10, and the positional information of the capsule endoscope 10 calculated by the computing unit 57 as described below.

The marker magnetic field detector 55 includes a filter unit 551 that shapes waveforms of the detection signals output from the sensing coils 32, an amplifier 552, an A/D converter 553 that generates detection data by applying A/D conversion processing to the detection signals, and an FFT processing unit 554 that extracts magnetic field information such as amplitude and a phase of the magnetic field by applying fast Fourier transform processing (hereinafter, FFT processing) to the detection data output from the A/D converter 553. The marker magnetic field detector 55 acquires detection values (magnetic field detection values) of the magnetic field including the marker magnetic field component and an environmental magnetic field component, by applying the above processing to the detection signals output from the sensing coils 32.

The environmental magnetic field detector 56 includes a filter unit 561 that shapes a waveform of the reference signal output from the reference coil 42, an amplifier 562, an A/D converter 563 that generates reference data by applying A/D conversion processing to the reference signal, and an FFT processing unit 564 that extracts the magnetic field information such as amplitude and a phase of the magnetic field by applying the FFT processing to the reference data output from the A/D converter 563. The environmental magnetic field detector 56 acquires a detection value (reference magnetic field detection value, hereinafter, reference value) of the environmental magnetic field, by applying the above processing to the reference signal output from the reference coil 42.

The computing unit 57 is configured by a central processing unit (CPU) and the like, for example, and reads the program stored in the storage unit 54 and performs predetermined calculation processing. To be specific, computing unit 57 includes a magnetic field correction unit 571, a position and direction calculation unit 572, and an image processing unit 573.

The magnetic field correction unit 571 corrects the magnetic field detection values output from the marker magnetic field detector 55 using the reference value of the environmental magnetic field output from the environmental magnetic field detector 56, and outputs the strength of the marker magnetic field from which an influence of the environmental magnetic field has been removed, using the corrected magnetic field detection values.

The position and direction calculation unit 572 calculates a position and a direction (inclinations in the X, Y, and Z directions of the long axis La of the capsule endoscope 10) of the capsule endoscope 10, based on the strength of the marker magnetic field output from the magnetic field correction unit 571. Hereinafter, information regarding the position and the direction of the capsule endoscope 10 is collectively referred to as positional information.

The image processing unit 573 generates display image data by applying predetermined image processing such as white balance processing, demosaicing, gamma conversion, smoothing (noise removal and the like) to the image data acquired through the receiving unit 51. The image data to which the image processing has been applied is stored in the storage unit 54 in association with the positional information calculated by the position and direction calculation unit 572.

The control unit 58 is configured from a central processing unit (CPU), for example, reads the program stored in the storage unit 54, and transfers instructions and data to the respective units that configure the position detecting device 50 to integrally control the operation of the position detecting device 50.

Figure 4:
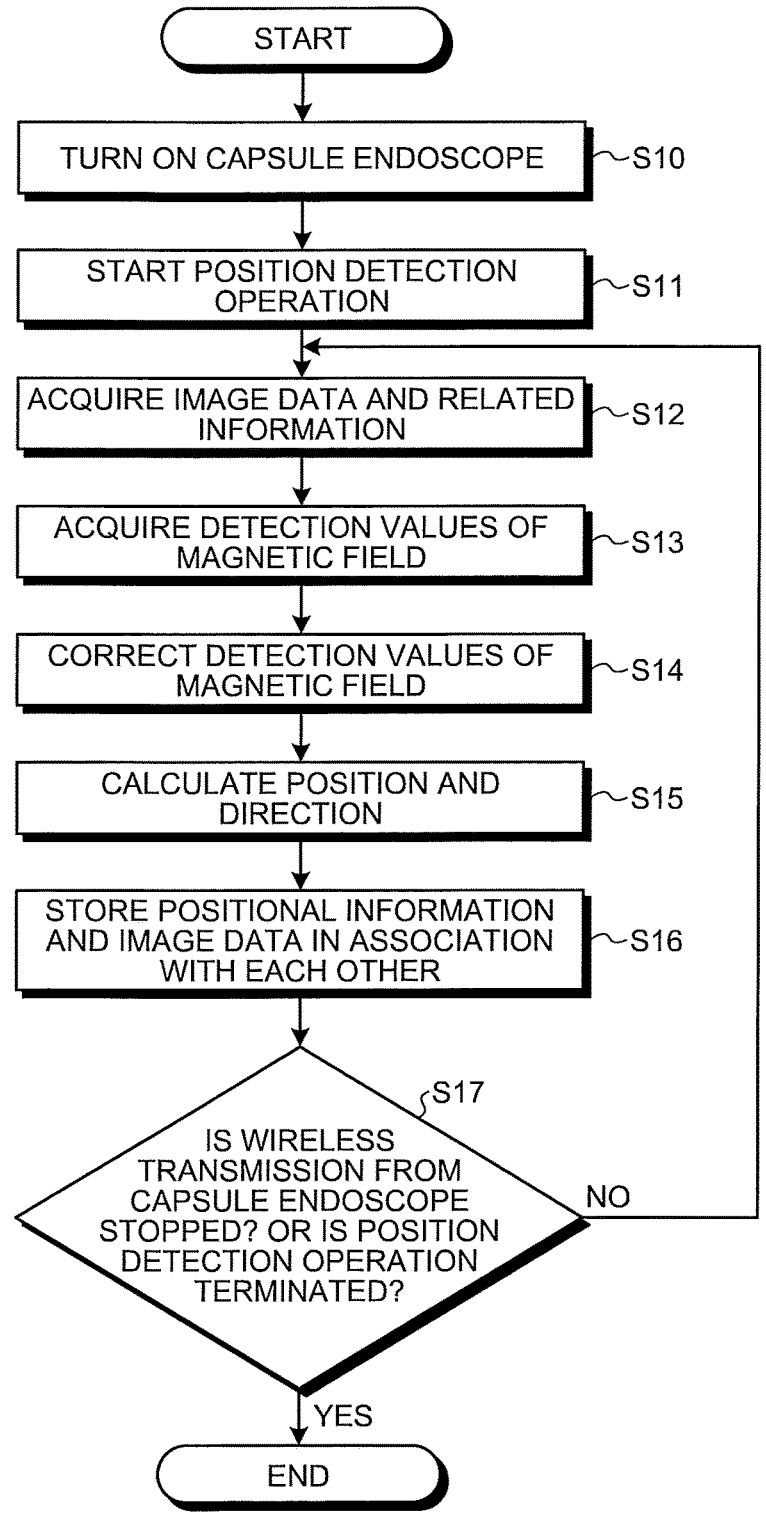
FIG. 4 is a flowchart illustrating an operation of the position detecting system according to FIG. 1.

Next, an operation of the position detecting system 1 will be described with reference to FIG. 4. FIG. 4 is a flowchart illustrating the operation of the position detecting system 1.

First, in step S10, the capsule endoscope 10 is turned ON. Accordingly, the capsule endoscope 10 causes the imaging section 113 to start an imaging operation and drives the magnetic field generation unit 14 to generate the marker magnetic field having a predetermined drive frequency from the marker coil 141. When the capsule endoscope 10 is introduced into the subject 100, the capsule endoscope 10 captures images while moving in the lumen by peristaltic movement, and wirelessly transmits the image data.

In step S11, when the instruction information of the start of the position detection operation is input from the operation input unit 52 to the position detecting device 50, in following step S12, the position detecting device 50 acquired the image data and the related information from the capsule endoscope 10. That is, the position detecting device 50 receives the radio signal transmitted from the capsule endoscope 10 through the receiving antenna 51a, and acquires the image data of the in-vivo image superimposed on the radio signal and the like by applying the demodulation processing and the like to the radio signal.

In step S13, the position detecting device 50 acquires the detection values of the magnetic field detected by the sensing coils 32 and the detection value of the magnetic field detected by the reference coil 42. To be specific, the marker magnetic field detector 55 takes in the detection signals from the sensing coils 32, and acquires detection values Bs of the strength of a drive frequency component of the marker magnetic field, by applying predetermined filter processing, amplification processing, the A/D conversion processing, and the FFT processing. The detection value Bs includes a marker magnetic field component Bm generated by the marker coil 141 and an environmental magnetic field component Bns.

The environmental magnetic field detector 56 takes in the reference signal from the reference coil 42 at the same timing as the marker magnetic field detector 55, and acquires a detection value (reference value) Br of the strength of a drive frequency component of the marker magnetic field by applying predetermined filter processing, amplification processing, the A/D conversion processing, and the FFT processing. The reference value Br is roughly made of the environmental magnetic field component.

In step S14, the computing unit 57 corrects the detection values Bs acquired by the marker magnetic field detector 55, using the detection value Br acquired by the environmental magnetic field detector 56. Here, as described above, the environmental magnetic field can be considered to be locally uniform, and thus the strength and the direction of the environmental magnetic field in the positions of the sensing coils 32 are nearly equal to the strength and the direction of the environmental magnetic field in the position of the reference coil 42. Therefore, the environmental magnetic field component Bns included in the magnetic field detected by the sensing coils 32 can be approximated with the reference value Br detected by the reference coil 42 (Bns≅Br). Therefore, the marker magnetic field component (strength) Bm from which the influence of the environmental magnetic field has been removed is given by the following formula (1):

$$Bm = Bs - Br \qquad (1)$$

In following step S15, the computing unit 57 calculates the position and the direction of the capsule endoscope 10 based on the detection values corrected in step S14, that is, the marker magnetic field components Bm from which the influence of the environmental magnetic field has been removed.

In step S16, the computing unit 57 stores the position and the direction (positional information) of the capsule endoscope 10 calculated by the position and direction calculation unit 572 and the image data to which the image processing has been applied by the image processing unit 573 to the storage unit 54 in association with each other.

In step S17, the control unit 58 determines whether the wireless transmission from the capsule endoscope 10 has been stopped, or whether the instruction information of the termination of the position detection operation has been input from the operation input unit 52 to the position detecting device 50. Note that the capsule endoscope 10 continues the wireless transmission of the image data and the generation of the marker magnetic field until the power supply unit 15 is turned OFF or the battery runs out.

When instruction information for stopping the wireless transmission or for termination of the position detection operation is not input (No in step S17), the operation of the position detecting system 1 returns to step S12. On the other hand, when the instruction information for stopping the wireless transmission or for termination of the position detection operation is input (Yes in step S17), the operation of the position detecting system 1 is terminated.

As described above, according to the first embodiment, the detection values of the magnetic field detected by the sensing coils 32 are corrected using the detection value (reference value) of the magnetic field detected by the reference coil 42. Therefore, the strength of the marker magnetic field from which the influence of the environmental magnetic field has been removed can be acquired. Therefore, by detecting the position and the direction of the capsule endoscope 10 based on the strength of the marker magnetic field, the position and the direction of the capsule endoscope 10 can be accurately detected.

Modification 1-1

Next, a modification 1-1 of the first embodiment of the present invention will be described.

Figure 5:
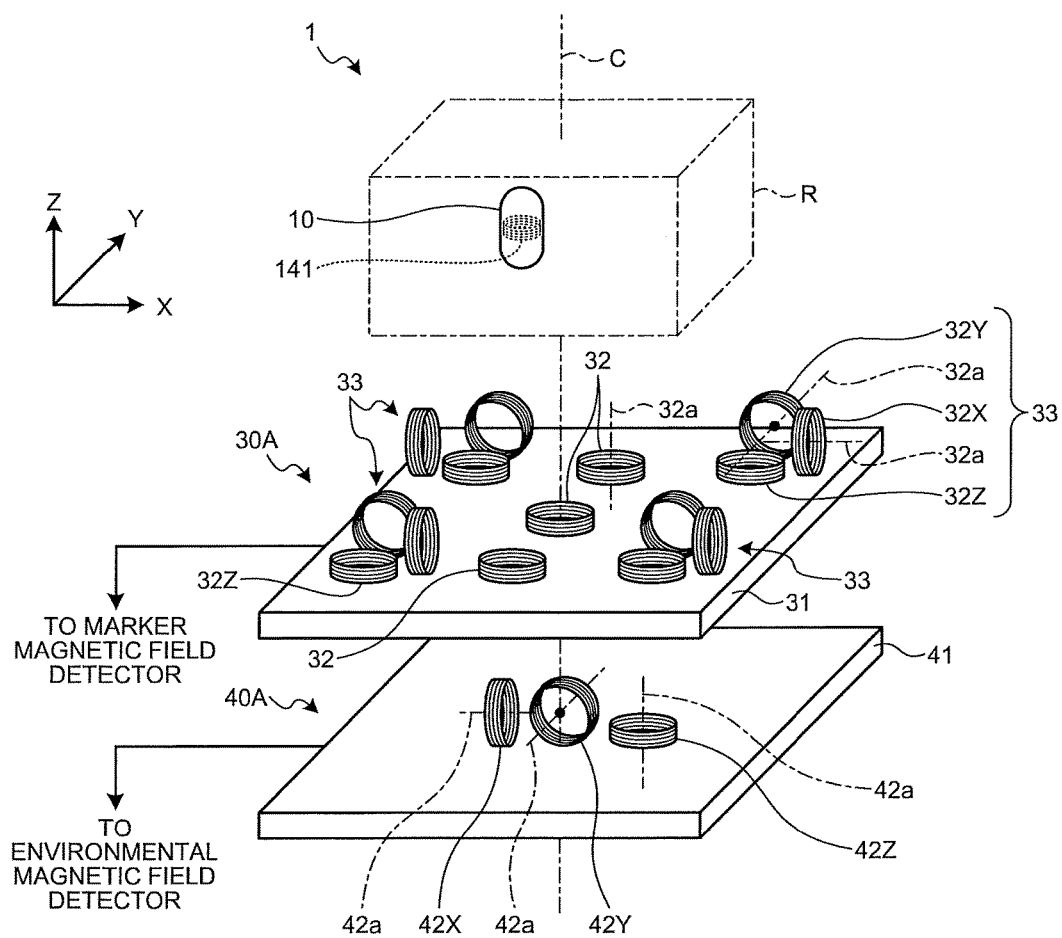
FIG. 5 is a schematic view illustrating a part of a configuration of a position detecting system according to a modification 1-1 of the first embodiment of the present invention.

FIG. 5 is a schematic view illustrating a configuration of a position detecting system according to a modification 1-1 of the first embodiment of the present invention.

To enhance position detection accuracy of a capsule endoscope 10, a part or all of sensing coils 32 illustrated in FIG. 3 may be changed to three-axis coils. For example, in a sensing coil unit 30A illustrated in FIG. 5, coil sets 33 that can detect a magnetic field in a three-dimensional manner are provided near four corners of a panel 31. Each of the coil sets 33 includes three sensing coils 32X, 32Y, and 32Z with central axes 32a respectively parallel to an X direction, a Y direction, and a Z direction. The sensing coils 32X, 32Y, and 32Z detect the magnetic field in the directions of the respective central axes 32a, and output detection signals. Note that configurations of the sensing coils 32X, 32Y, and 32Z are similar to that of the sensing coil 32 illustrated in FIG. 3.

In this case, in a reference coil unit 40A that outputs a reference signal, three reference coils 42X, 42Y, and 42Z with central axes 42a respectively parallel to the X direction, the Y direction, and the Z direction are arranged in accordance with the directions of the sensing coils 32X, 32Y, and 32Z. The reference coils 42X, 42Y, and 42Z detect an environmental magnetic field in the directions of the central axes 42a, and output reference signals. Note that configurations of the reference coils 42X, 42Y, and 42Z are similar to that of the reference coil 42 illustrated in FIG. 3.

The reference coils 42X, 42Y, and 42Z are preferably arranged symmetrical (line-symmetrical or point-symmetrical) with respect to a central axis C. In FIG. 5, the reference coils 42X, 42Y, and 42Z are arranged on a central line of a panel 41, the central line passing through the central axis C. More preferably, these reference coils 42X, 42Y, and 42Z are arranged close to the central axis C. If these reference coils are arranged on the central axis C, distances between the reference coils 42X, 42Y, and 42Z and the sensing coils become roughly uniform, and no sensing coils are extremely close to or distant from the reference coils. Therefore, even if local change is caused in the environmental magnetic field, an influence thereof can be suppressed.

When the coil sets 33 are arranged as described above, in correcting detection values Bs of the magnetic field in step S14 (see FIG. 4), calculation is performed using detection values (reference values) Br of the reference signals output from the reference coils 42 respectively facing the same directions as the sensing coils 32X, 32Y, and 32Z. That is, the detection value Br of the magnetic field based on the reference coil 42X is subtracted from the detection value Bs of the magnetic field by the sensing coil 32X. The same applies to the sensing coils 32Y and 32Z. Accordingly, correction according to the direction of the environmental magnetic field can be performed.

Modification 1-2

Next, a modification 1-2 of the first embodiment of the present invention will be described.

An arrangement of a reference coil unit 40 is not limited to the above-described first embodiment and various arrangements are possible as long as SN ratios in reference coils 42 to a marker magnetic field can be made smaller than SN ratios in sensing coils 32.

For example, the reference coil unit 40 may be arranged at an opposite side to a sensing coil unit 30 with respect to a targeted region R (above the targeted region R in FIG. 1).

Alternatively, reference coils 42 may be arranged above a panel 31 of the sensing coil unit 30. In this case, the reference coils 42 may be preferably arranged outside the sensing coils 32 with respect to a region on the panel 31, on which the targeted region R is projected.

Second Embodiment

Next, a second embodiment of the present invention will be described.

Figure 6:
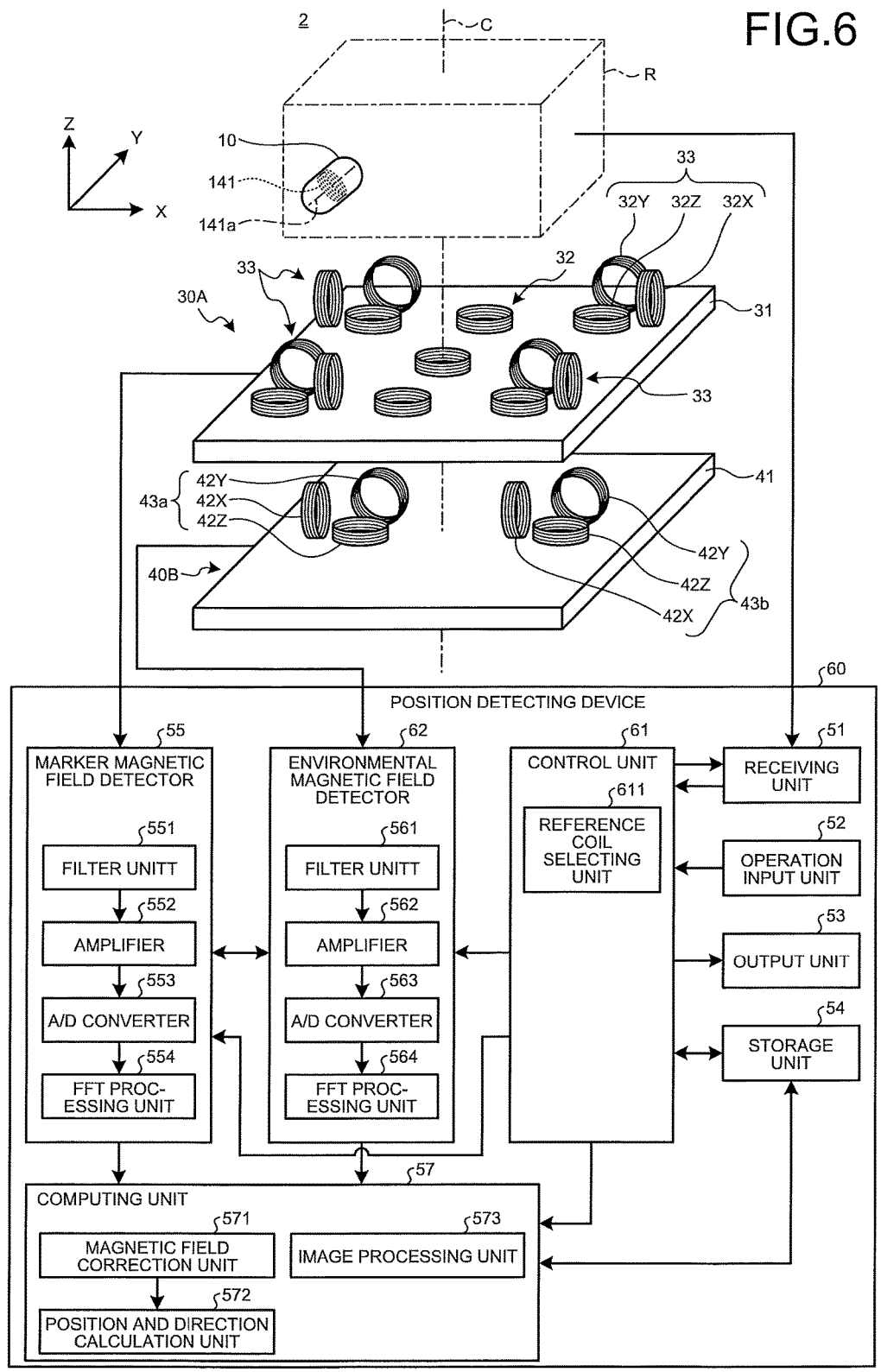
FIG. 6 is a schematic view illustrating a configuration of a position detecting system according to a second embodiment of the present invention.

FIG. 6 is a schematic view illustrating a configuration of a position detecting system according to a second embodiment of the present invention. As illustrated in FIG. 6, a position detecting system 2 according to the second embodiment includes a capsule endoscope 10, a sensing coil unit 30A, a reference coil unit 40B, and a position detecting device 60. Among them, configurations and operations of the capsule endoscope 10 and the sensing coil unit 30A are similar to those of the first embodiment and its modification 1-1.

The reference coil unit 40B includes a panel 41, and a plurality of coil sets 43a and 43b (two coil sets in FIG. 6) arranged on the panel 41. Each of the coil sets 43a and 43b is made of three reference coils 42X, 42Y, and 42Z with respective central axes 42a parallel to an X direction, a Y direction, and a Z direction.

The plurality of coil sets 43a and 43b are arranged symmetrical with respect to a central axis C. Accordingly, as described below, selection of the coil set 43a or 43b according to a position of the capsule endoscope 10 in a targeted region R becomes easy.

The position detecting device 60 includes a control unit 61 and an environmental magnetic field detector 62, in place of a control unit 58 and an environmental magnetic field detector 56 illustrated in FIG. 1, respectively. Between them, the control unit 61 includes a reference coil selecting unit 611 that selects a coil set to be used for correction of detection values of a magnetic field detected by the sensing coil unit 30A, of the plurality of coil sets 43a and 43b.

The environmental magnetic field detector 62 takes in detection signals from the reference coils 42 included in the coil set selected by the reference coil selecting unit 611, and acquires detection values of an environmental magnetic field in the position of the selected coil set, by applying predetermined processing to the detection signals. Note that processing for the detection signals is similar to that of the first embodiment.

Next, an operation of the position detecting system 2 will be described. The operation of the position detecting system 2 is similar to that of the first embodiment (see FIG. 4) as a whole, and a detailed operation in step S13 is different from that of the first embodiment.

That is, in step S13 following step S12, the position detecting device 60 acquires detection values of the magnetic field respectively detected by the sensing coil unit 30A and the reference coil unit 40B. At this time, the reference coil selecting unit 611 selects a coil set most distant from the position of the capsule endoscope 10, of the coil sets 43a and 43b, based on positional information of the previously detected capsule endoscope 10. In other words, the reference coil selecting unit 611 selects a coil set having a smallest influence of a marker magnetic field generated by a marker coil 141. For example, in the case of FIG. 6, the coil set 43b more distant from the capsule endoscope 10 is selected.

The environmental magnetic field detector 62 takes in detection signals (reference signals) from the reference coils 42X, 42Y, and 42Z included in the selected coil set 43b, and acquires reference values of the magnetic field in X, Y, and Z directions, by applying predetermined processing. In these reference values, marker magnetic field components are smallest and environmental magnetic field components are largest in the coil sets including the non-selected coil set 43a. That is, an SN ratio is low. Note that an operation of a marker magnetic field detector 55 is similar to that of the first embodiment.

In following step S14, a computing unit 57 corrects the detection values of the magnetic field detected by the sensing coil unit 30A, using the reference values acquired in step S13. Operations of step S15 and subsequent steps are similar to those of the first embodiment and the modification 1-1.

Here, as described above, the environmental magnetic field has small local change. However, correlation of the environmental magnetic field between the sensing coil unit 30A and the reference coil unit 40B becomes smaller, and a possibility of causing a difference in the strength and the direction is increased, as the sensing coil unit 30A and the reference coil unit 40B are more distant. As a result, an error of a marker magnetic field component Bm given by the formula (1) may become large. Therefore, it is preferable to arrange the reference coil unit 40B as close as possible to the sensing coil unit 30A. In contrast, if the reference coil unit 40B is brought close to the sensing coil unit 30A, the reference coil unit 40B also gets close to the targeted region R. Therefore, the reference coils 42X, 42Y, and 42Z easily detect the marker magnetic field, and an SN ratio of the marker magnetic field component Bm given by the formula (1) may be decreased.

Therefore, the second embodiment focuses on a fact that the strength of the marker magnetic field in positions of the reference coils 42X, 42Y, and 42Z is changed according to relative positions between the marker coil 141, and the reference coils 42X, 42Y, and 42Z, and decreases the marker magnetic field component included in the reference values, by selecting the reference coils 42X, 42Y, and 42Z (the coil set 43b in the case of FIG. 6) most distant from the capsule endoscope 10. By correcting the detection values of the sensing coils 32 using such reference values, the environmental magnetic field component can be appropriately removed from the detection values.

As described above, according to the second embodiment, the reference coil unit 40B can be arranged close to the sensing coil unit 30A while suppressing the marker magnetic field detected by the reference coils 42X, 42Y, and 42Z. Therefore, a decrease in a size of the position detecting system becomes possible while maintaining position detection accuracy of the capsule endoscope 10.

Modification 2-1

Next, a modification 2-1 of the second embodiment of the present invention will be described.

In a position detecting system 2 illustrated in FIG. 6, directions of a marker magnetic field detected by reference coils 42X, 42Y, and 42Z are changed according to relative positions between the reference coils 42X, 42Y, and 42Z and a marker coil 141. Therefore, a reference coil selecting unit 611 may select a coil set from which reference signals are to be taken in next, from among coil sets 43a and 43b, based on information on a direction of a previously detected capsule endoscope 10. In this case, the reference coil selecting unit 611 selects a coil set most distant from an extension line of a central axis 141a of a marker coil 141. This is because the marker magnetic field becomes strongest in the extended line of the central axis 141a of the marker coil 141.

Modification 2-2

Next, a modification 2-2 of the second embodiment of the present invention will be described.

A reference coil selecting unit 611 may select a coil set from which reference signals are to be taken in next, based on previously acquired reference values. In this case, the reference coil selecting unit 611 selects a coil set in which a total of the reference values or a representative value (a maximum value, a minimum value, or the like), of the reference values in X, Y, and Z three directions, becomes minimum. Alternatively, the reference coil selecting unit 611 may select a coil set in which the total or the representative value of the reference values becomes a predetermined threshold or less.

Modification 2-3

Next, a modification 2-3 of the second embodiment of the present invention will be described.

If the plurality of sensing coils 32 is arranged so as to be oriented at the same direction like the first embodiment (FIG. 1), a plurality of reference coils 42 facing the same direction as the sensing coils 32 is arranged at a side of a reference coil unit, and a reference coil selecting unit 611 may select one reference coil 42 from which a reference signal is to be taken in. A method of selecting the reference coil 42 is similar to that of the second embodiment, the modification 2-1, or the modification 2-2.

Third Embodiment

Next, a third embodiment of the present invention will be described.

Figure 7:
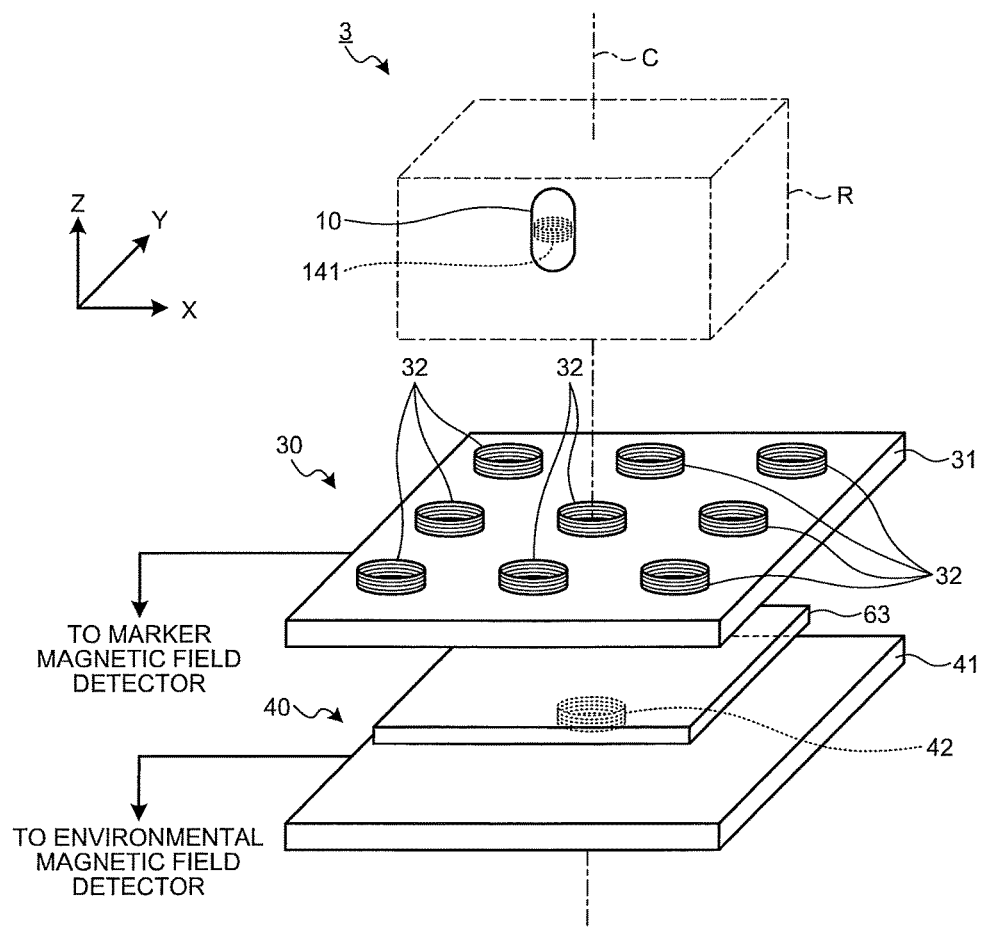
FIG. 7 is a schematic view illustrating a part of a configuration of a position detecting system according to a third embodiment of the present invention.

FIG. 7 is a schematic view illustrating a part of a configuration of a position detecting system according to a third embodiment of the present invention. As illustrated in FIG. 7, in a position detecting system 3 according to the third embodiment, a magnetic shield 63 is further provided between a sensing coil unit 30 and a reference coil unit 40, compared with the position detecting system 1 (see FIG. 3) according to the first embodiment. The magnetic shield 63 is a plate member made of a ferromagnetic body such as iron or nickel, and shields a marker magnetic field generated by a capsule endoscope 10 (marker coil 141) against the reference coil unit 40.

Here, as described above, it is preferable that the sensing coil unit 30 and the reference coil unit 40 are arranged as close as possible. Unfortunately, however, because the reference coil unit 40 gets close to a targeted region R if the reference coil unit 40 is brought close to the sensing coil unit 30, a reference coil 42 may easily detect the marker magnetic field.

In order to address such a situation, in the third embodiment, the magnetic shield 63 is provided to shield the marker magnetic field against the reference coil 42. Accordingly, the reference coil unit 40 can be arranged close to the sensing coil unit 30 without causing the reference coil 42 to detect the marker magnetic field. As a result, it becomes unnecessary to arrange the reference coil unit 40 sufficiently distant from the targeted region R. Therefore, the position detecting system 3 can be downsized.

Fourth Embodiment

Next, a fourth embodiment of the present invention will be described.

Figure 8:
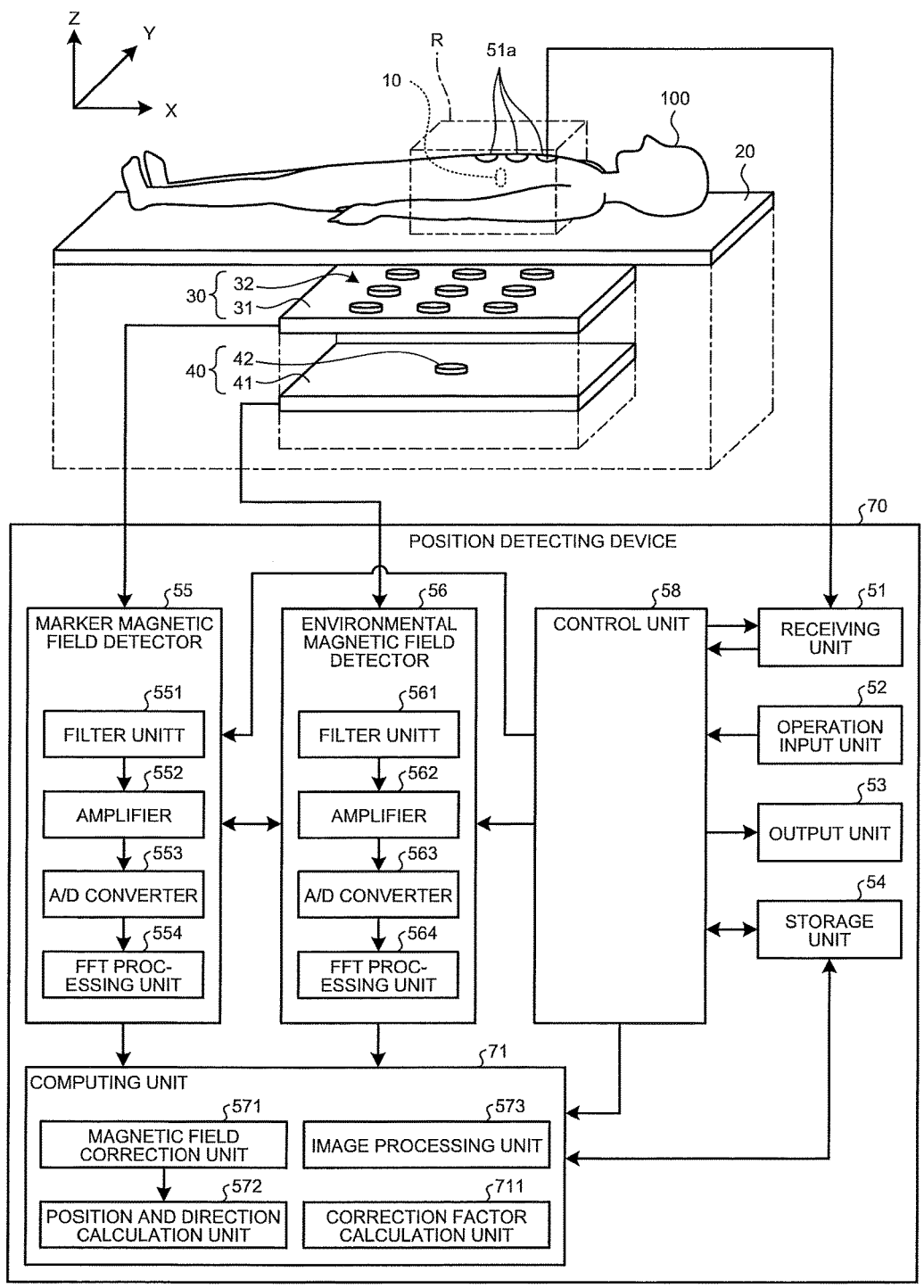
FIG. 8 is a schematic view illustrating a configuration of a position detecting system according to a fourth embodiment of the present invention.

FIG. 8 is a schematic view illustrating a configuration of a position detecting system according to a fourth embodiment of the present invention. As illustrated in FIG. 8, a position detecting system 4 according to the fourth embodiment includes a position detecting device 70, in place of a position detecting device 50 illustrated in FIG. 1. Note that configurations of respective units of the position detecting system 4 except the position detecting device 70 are similar to those of the first embodiment.

The position detecting device 70 includes a computing unit 71 further including a correction factor calculation unit 711, compared with the computing unit 57 illustrated in FIG. 1. Configurations and operations of respective units of the position detecting device 70 except the computing unit 71 are similar to those of the first embodiment.

Here, typically, an environmental magnetic field has small local change, but correlation of the environmental magnetic field between sensing coils 32 and a reference coil 42 becomes smaller, and a possibility of causing a difference in strength and a direction of the environmental magnetic field is increased, as the sensing coils 32 and the reference coil 42 are more distant. Further, in a case where an intervention such as metal exists near the sensing coils 32 or the reference coil 42, the environmental magnetic field may be largely changed around the intervention. Further, in a case of providing a magnetic shield like the third embodiment, an ambient environmental magnetic field may be affected, depending on an installation position or a direction of the magnetic shield. In these cases, a reference value Br based on a reference signal, which is taken in from the reference coil 42, cannot be considered to be equal to an environmental magnetic field component Bns at the positions of the sensing coils 32. Therefore, in correction processing by the formula (1), the environmental magnetic field component cannot be appropriately cancelled from detection values of the magnetic field detected by the sensing coils 32, and position detection accuracy of the capsule endoscope 10 is decreased.

Therefore, in the fourth embodiment, the correction factor calculation unit 711 is provided in the computing unit 71, and acquires a correction factor based on the difference in the environmental magnetic field between the sensing coils 32 and the reference coil 42 in advance and corrects the detection values of the magnetic field detected by the sensing coils 32, using the correction factor.

Figure 9:
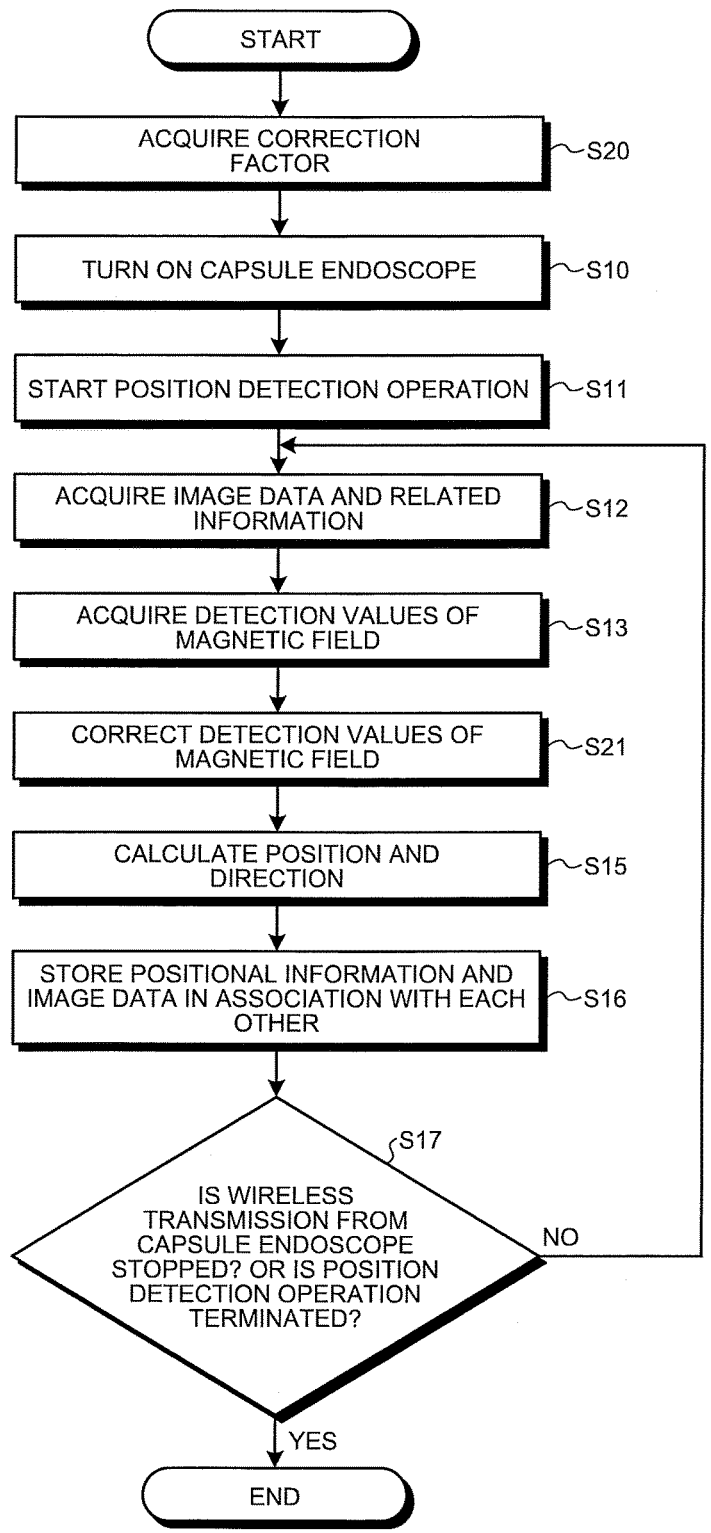
FIG. 9 is a flowchart illustrating an operation of the position detecting system illustrated in FIG. 8.

FIG. 9 is a flowchart illustrating an operation of the position detecting system 4.

First, prior to an examination using the capsule endoscope 10, in step S20, the computing unit 71 acquires a ratio of detection values of the environmental magnetic field between the sensing coils 32 and the reference coil 42 as the correction factor. Acquisition of the correction factor is performed in a state where no marker magnetic field is generated, for example, in a state where a power supply of the capsule endoscope 10 is OFF or in a state in which the capsule endoscope 10 does not exist in the targeted region R.

To be specific, the computing unit 71 acquires a detection value $Bs_0$ of the magnetic field detected by the sensing coil 32 and a detection value $Br_0$ of the magnetic field detected by the reference coil 42, similarly to step S13 described above. These detection values $Bs_0$ and $Br_0$ respectively express the strength of the environmental magnetic field in the positions of the sensing coil 32 and the reference coil 42. The correction factor calculation unit 711 calculates a ratio $Bs_0/Br_0$ of these detection values $Bs_0$ and $Br_0$, and stores the ratio in a storage unit 54 as a correction factor K. Calculation of the correction factor K is executed for each of the sensing coils 32.

Here, acquisition of the correction factor K may be automatically executed when the power supply of the position detecting device 70 is turned ON, for example. Alternatively, an operation switch for inputting an instruction of calibration may be provided in an operation input unit 52, and acquisition of the correction factor K may be executed by an operation of the operation switch by a user at any time. Operations of following steps S10 to S13 are similar to those of the first embodiment.

In step S21 following step S13, the magnetic field correction unit 571 corrects the detection value Bs acquired by a marker magnetic field detector 55, using the correction factor K of each sensing coil 32. The detection value after correction, that is, a marker magnetic field component Bm from which an influence of the environmental magnetic field has been removed is given by the following formula (2):

$$Bm = Bs - K \cdot Br \quad (2)$$

That is, by multiplying the detection value Br of the magnetic field by the correction factor K, the strength of the environmental magnetic field in the position of the reference coil 42 is adjusted to the strength of the environmental magnetic field in the position of the sensing coil 32. Operations of following steps S15 to S17 are similar to those of the first embodiment.

As described above, according to the fourth embodiment, after the difference in the environmental magnetic field in the position of the sensing coil 32 and the environmental magnetic field in the position of the reference coil 42 is suppressed using the correction factor K acquired in advance, the influence of the environmental magnetic field is removed from the detection value Bs of the magnetic field detected by the sensing coil 32. Therefore, position detection accuracy of the capsule endoscope 10 can be further improved.

Note that, in step S20, only one correction factor K may be calculated for one of the plurality of sensing coils 32 (for example, for the central sensing coil 32). In this case, in step S21, magnetic field detection values in all of the sensing coils 32 are corrected using the one correction factor K. This is effective in a case where the distance between the sensing coil unit 30 and the reference coil unit 40 is distant, but variation of the environmental magnetic field between the units 30 and 40 is small.

Alternatively, the plurality of sensing coils 32 may be divided into a plurality of areas, and one correction factor K may be calculated for each area. In this case, correction is performed for the magnetic field detection values in the sensing coils 32 in one area, using the correction factor calculated for the one area. This has an advantage of simplifying the calculation processing of the correction factor K in a case where the number of the sensing coils 32 is large.

Modification 4-1

Next, a modification 4-1 of the fourth embodiment of the present invention will be described.

The above-described fourth embodiment may be applied to the modification 1-1 (see FIG. 5) of the first embodiment. In this case, a correction factor may just be calculated according to magnitude (an absolute value) of a vector having, as components, detection values of a magnetic field by respective directions of sensing coils 32X, 32Y and 32Z included in each of coil sets 33, and magnitude (an absolute value) of a vector having, as components, detection values of a magnetic field by respective directions of reference coils 42X, 42Y and 42Z.

Alternatively, the correction factor is calculated between the sensing coils 32X, 32Y, and 32Z in each of the coil sets 33, and the reference coils 42X, 42Y, and 42Z respectively in the same directions, and detection values of the magnetic field of the sensing coils 32X, 32Y, and 32Z may be corrected by the X, Y, and Z directions.

According to the modification 4-1, even if not only the strength but also the direction of the environmental magnetic field is changed due to an influence of an intervention, the strength and the direction of the environmental magnetic field in the positions of the sensing coils 32X, 32Y, and 32Z can be accurately estimated using the detection values (reference values) of the magnetic field of the reference coils 42X, 42Y, and 42Z and the correction factor. Therefore, the position of the capsule endoscope 10 can be accurately detected.

Modification 4-2

Next, a modification 4-2 of the fourth embodiment of the present invention will be described.

Figure 10:
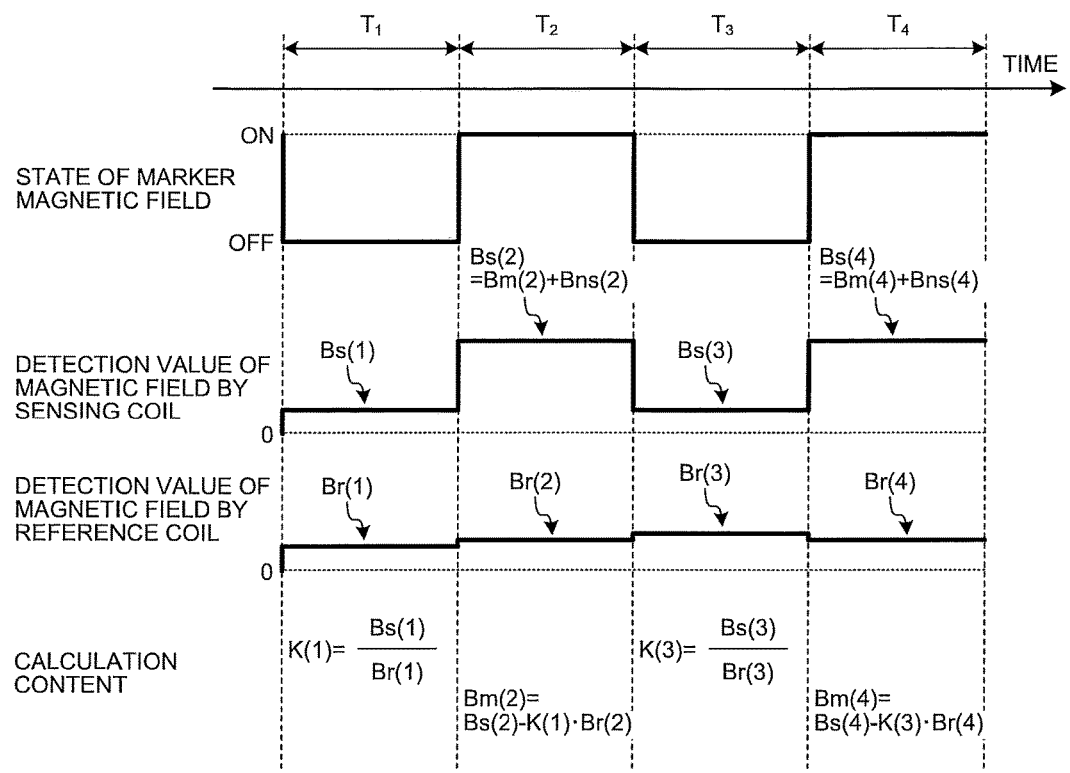
FIG. 10 is a chart illustrating operation timing of respective units of a position detecting system according to a modification 4-2 of the fourth embodiment of the present invention.

FIG. 10 is a chart illustrating operation timing of respective units of a position detecting system according to the modification 4-2. As illustrated in FIG. 10, in a capsule endoscope 10, an alternating magnetic field may be intermittently generated by intermittently supplying electricity to and driving a marker coil 141. In this case, a correction factor K is acquired while a marker magnetic field is OFF, and detection values of the magnetic field detected by sensing coils 32 are corrected using a previously acquired correction factor K while the marker magnetic field is ON.

For example, as illustrated in FIG. 10, consider a case of switching ON/OFF of the marker magnetic field in every time $\Delta T$. In the description below, lengths of periods $T_1$, $T_2$, $T_3$, and $T_4$ are $\Delta T$. In the period $T_1$ in which the marker magnetic field is OFF, a computing unit 71 calculates a correction factor $K(1)=Bs(1)/Br(1)$ from a detection value Bs (1) of the magnetic field detected by the sensing coil 32 and a detection value Br (1) of the environmental magnetic field by a reference coil 42.

In following period $T_2$, the marker magnetic field is turned ON. During this period, the computing unit 71 calculates a marker magnetic field component Bm (2) given by the above formula (2), from a detection value Bs (2) of the magnetic field detected by the sensing coil 32, a detection value Br (2) of the environmental magnetic field by the reference coil 42, and the previously calculated correction factor K (1). Further, the computing unit 71 calculates the position and the direction of the capsule endoscope 10 based on the marker magnetic field component Bm (2).

In a following period $T_3$, the marker magnetic field becomes OFF. During this period, the computing unit 71 calculates a correction factor $K(3)=Bs(3)/Br(3)$ from a detection value Bs (3) of the magnetic field detected by the sensing coil 32 and a detection value Br (3) of the environmental magnetic field by the reference coil 42.

In a following period $T_4$, the marker magnetic field becomes ON. During this period, the computing unit 71 calculates a marker magnetic field component Bm (4) given by the formula (2) from a detection value Bs (4) of the magnetic field detected by the sensing coil 32, a detection value Br (4) of the environmental magnetic field by the reference coil 42, and the previously calculated correction factor K(3), and further calculates the position and the direction of the capsule endoscope 10.

By repeating such operations, the correction factor K(i) (i=1, 2, . . . ) is updated in every period $2\Delta T$, and during the period in which the marker magnetic field is ON, calculation using the latest correction factor K (n) is always performed. Accordingly, even if temporal change is caused in the environmental magnetic field, the influence due to the change can be suppressed to the minimum. Therefore, the environmental magnetic field component Bns (i) is accurately removed from the detection value Bs (i) of the magnetic field detected by the sensing coil 32, and the position detection accuracy of the capsule endoscope 10 can be improved.

Further, according to the modification 4-2, an effect to suppress power consumption in the capsule endoscope 10 can be obtained by intermittently driving the marker coil 141.

Modification 4-3

Next, a modification 4-3 of the fourth embodiment of the present invention will be described.

In a case of continuously driving a marker coil 141, unlike the modification 4-2, timing to acquire a correction factor K may be set as follows in examples (1) to (4).

(1) After start of an examination by a capsule endoscope 10, a subject 100 into which the capsule endoscope 10 is introduced is temporarily kept away from a targeted region R. For example, a slide-type moving mechanism may be provided in a bed 20, and the bed 20 may be slid in converting a body posture of the subject 100 and the subject 100 may be retracted from the targeted region R. During this period, the correction factor K is acquired.

(2) A magnetic shield is temporarily inserted into between the targeted region R and a sensing coil unit 30, and the marker magnetic field is shielded against the sensing coil unit 30. During this period, the correction factor K is obtained.

(3) A cancel coil that can cancel the marker magnetic field is arranged between the targeted region R and the sensing coil unit 30, and short-circuit and open are switched periodically or at any time. Then, while the cancel coil is short-circuited, the correction factor K is acquired.

(4) The correction factor K is successively updated only for a sensing coil 32 in which the strength of the marker magnetic field becomes approximately zero, the marker magnetic field being changed according to the position of the capsule endoscope 10, of the plurality of sensing coils 32 arranged on a panel 31.

Modification 4-4

Next, a modification 4-4 of the fourth embodiment of the present invention will be described.

After start of an examination using a capsule endoscope, a correction factor K may be acquired after a capsule endoscope is guided to a position where sensing coils 32 and a reference coil 42 cannot detect a marker magnetic field, or a position where detection values become a threshold Th (see the first embodiment). Hereinafter, a position detecting system that can operate and guide a capsule endoscope will be described.

Figure 11:
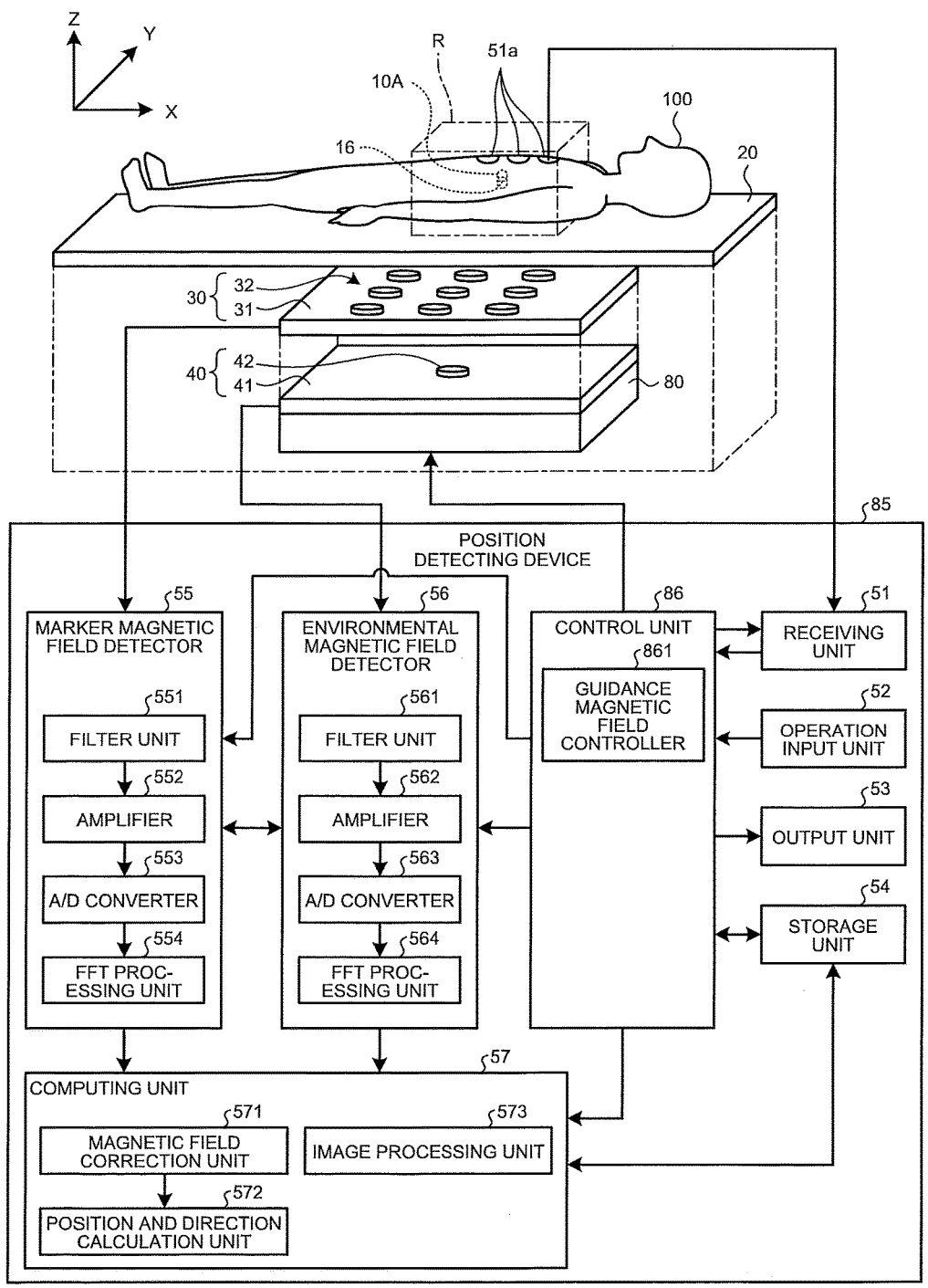
FIG. 11 is a schematic view illustrating a position detecting system according to a modification 4-4 of the fourth embodiment of the present invention.

FIG. 11 is a schematic view illustrating a configuration of a position detecting system according to a modification 4-4. A position detecting system 5 illustrated in FIG. 11 includes a capsule endoscope 10A, a sensing coil unit 30, a reference coil unit 40, a guidance magnetic field generation unit 80 that generates a magnetic field for guiding the capsule endoscope 10A, and a position detecting device 85. Among them, configurations and operations of the sensing coil unit 30 and the reference coil unit 40 are similar to those of the first embodiment.

Figure 12:
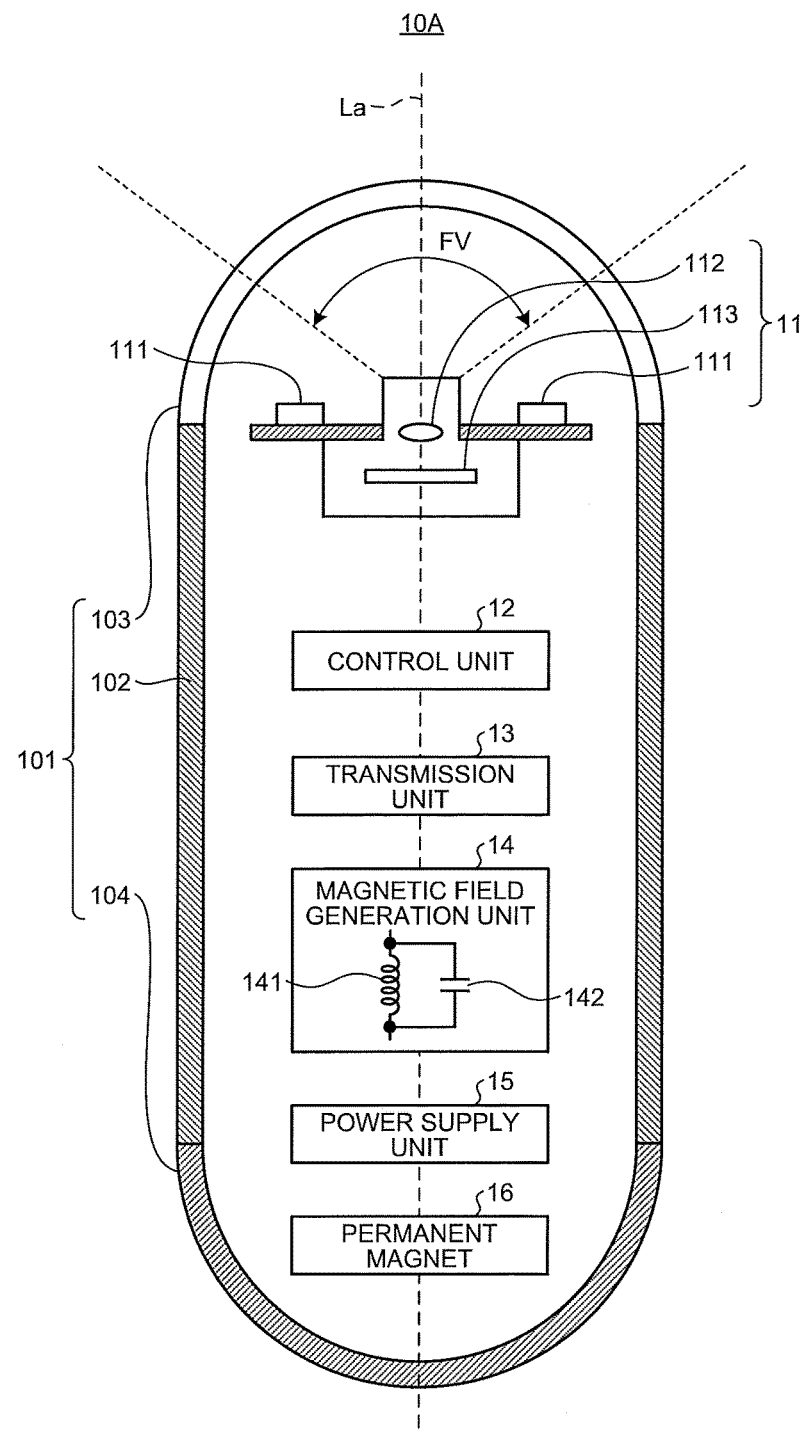
FIG. 12 is a schematic view illustrating an example of an internal configuration of a capsule endoscope illustrated in FIG. 11.

FIG. 12 is a schematic view illustrating an example of an internal configuration of the capsule endoscope 10A. The capsule endoscope 10A is obtained such that a permanent magnet 16 is fixed and arranged in a capsule endoscope 10 illustrated in FIG. 2. The permanent magnet 16 is arranged such that a magnetizing direction becomes perpendicular to a long axis La of the capsule endoscope 10A, for example. The permanent magnet 16 is operated following a magnetic field applied from an outside. As result, guidance of the capsule endoscope 10A by the guidance magnetic field generation unit 80 is realized.

Figure 13:
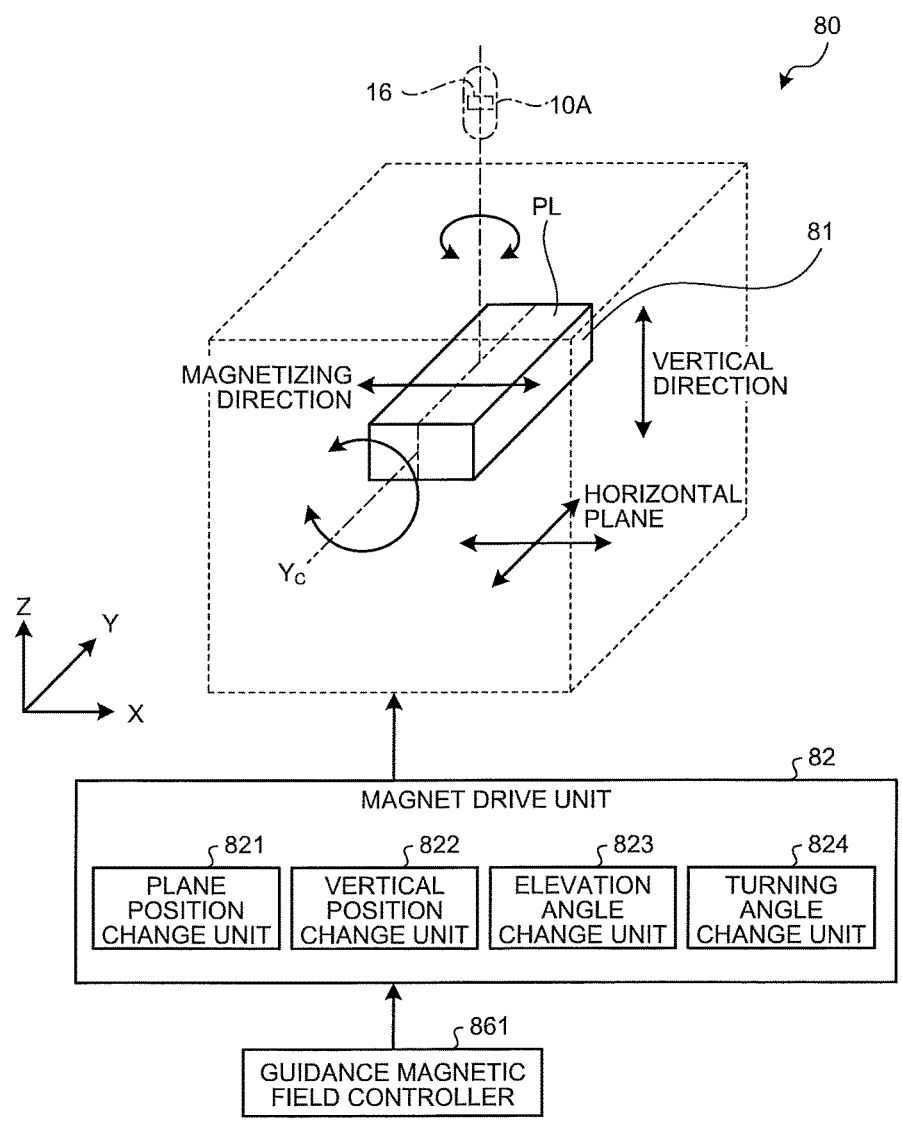
FIG. 13 is a schematic view illustrating a configuration example of a guidance magnetic field generation unit illustrated in FIG. 11.

FIG. 13 is a schematic view illustrating a configuration example of the guidance magnetic field generation unit 80. As illustrated in FIG. 13, the guidance magnetic field generation unit 80 generates a guidance magnetic field for changing a position and a direction of the capsule endoscope 10A, in a space including a targeted region R. To be specific, the guidance magnetic field generation unit 80 includes an extracorporeal permanent magnet 81 that generates a magnetic field, and a magnet drive unit 82 that changes a position and a posture of the extracorporeal permanent magnet 81.

The extracorporeal permanent magnet 81 is preferably configured from a bar magnet having a rectangular parallelepiped shape, and traps the capsule endoscope 10A in a region facing one plane PL in four planes parallel to the own magnetizing direction.

The magnet drive unit 82 includes a plane position change unit 821, a vertical position change unit 822, an elevation angle change unit 823, and a turning angle change unit 824. The plane position change unit 821 translates the extracorporeal permanent magnet 81 in an XY plane. The vertical position change unit 822 translates the extracorporeal permanent magnet 81 along a Z direction. The elevation angle change unit 823 rotates the extracorporeal permanent magnet 81 around a Yc axis in a vertical plane including the magnetizing direction of the extracorporeal permanent magnet 81. The turning angle change unit 824 rotates the extracorporeal permanent magnet 81 with respect to an axis of a vertical direction that passes through a center of the extracorporeal permanent magnet 81.

The extracorporeal permanent magnet 81 is moved and rotated by such a magnet drive unit 82, so that the capsule endoscope 10A trapped in the magnetic field generated by the extracorporeal permanent magnet 81 is moved in the subject 100, and changes an imaging visual field FV (see FIG. 12).

The position detecting device 85 includes a control unit 86 including a guidance magnetic field controller 861. The guidance magnetic field controller 861 generates and outputs control information for controlling the magnet drive unit 82 according to an operation signal input from an operation input unit 52.

In acquiring the correction factor K in the position detecting system 5, the operation input unit 52 is operated, and the capsule endoscope 10A is guided to a position where a marker magnetic field detected by sensing coils 32 and a reference coil 42 is minimized or becomes a threshold Th or less. Note that the position of the capsule endoscope 10A at this time is determined in advance before the start of the examination of the capsule endoscope 10A. Here, during guidance of the capsule endoscope 10A, the permanent magnet 16 in the capsule endoscope 10A and the extracorporeal permanent magnet 81 of the guidance magnetic field generation unit 80 are moved. Therefore, the sensing coils 32 and the reference coil 42 detect the magnetic field including magnetic field components of these permanent magnet. However, only a marker magnetic field component can be extracted from the detected magnetic field by a marker magnetic field detector 55. Therefore, in this state, detection values of the magnetic field detected by the sensing coils 32 and the reference coil 42 may just be acquired and the correction factor K may be calculated.

Fifth Embodiment

Next, a fifth embodiment of the present invention will be described.

Figure 14:
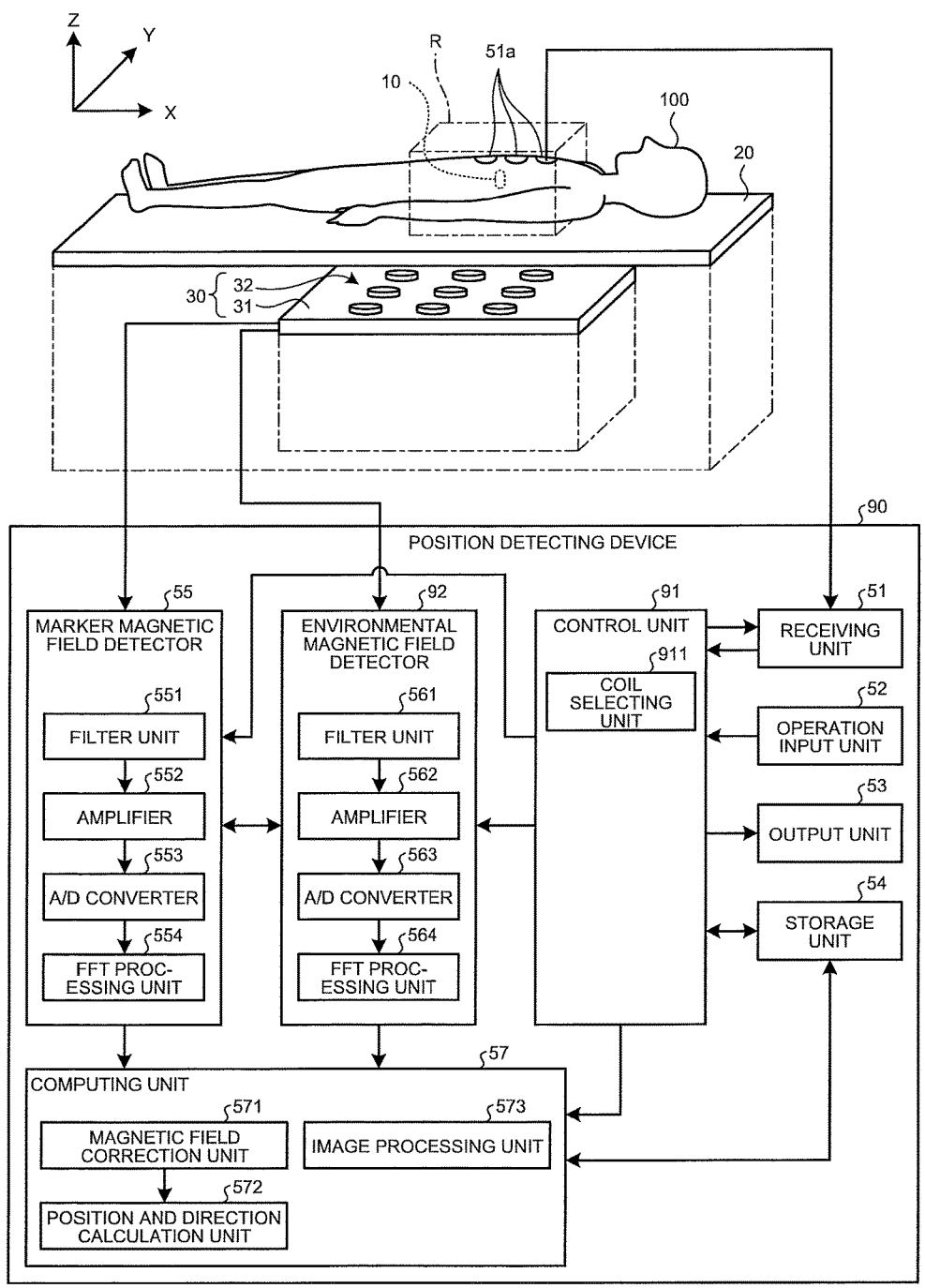
FIG. 14 is a schematic view illustrating a configuration of a position detecting system according to a fifth embodiment of the present invention.

FIG. 14 is a schematic view illustrating a configuration of a position detecting system according to a fifth embodiment of the present invention. As illustrated in FIG. 14, a position detecting system 6 according to the fifth embodiment includes a capsule endoscope 10, a sensing coil unit 30, and a position detecting device 90. Among them, a configuration and an operation of the capsule endoscope 10 is similar to those of the first embodiment. Further, a configuration of the sensing coil unit 30 is similar to that of the first embodiment.

However, in the fifth embodiment, detection signals output from sensing coils 32 included in the sensing coil unit 30 are also used as reference signals.

The position detecting device 90 includes a control unit 91 and an environmental magnetic field detector 92, in place of a control unit 58 and an environmental magnetic field detector 56, illustrated in FIG. 1, respectively. The control unit 91 includes a coil selecting unit 911 that takes in a detection signal used as a reference signal, from among a plurality of sensing coils 32. Further, the environmental magnetic field detector 92 takes in the detection signal from the sensing coil 32 selected by the coil selecting unit 911, and acquires a detection value of an environmental magnetic field in the position of the selected sensing coil 32. Note that configurations and operations of respective units of the position detecting device 90 except the control unit 91 and the environmental magnetic field detector 92 are similar to those of the first embodiment.

Next, an operation of the position detecting system 6 will be described. The operation of the position detecting system 6 is similar to that of the first embodiment (see FIG. 4) as a whole, and a detailed operation in step S13 is different from that of the first embodiment.

In step S13 following step S12, the position detecting device 90 acquires the detection value of the magnetic field detected by the sensing coil unit 30. At this time, the coil selecting unit 911 selects the sensing coil 32 most distant from the capsule endoscope 10, of the plurality of sensing coils 32, based on positional information of the previously detected capsule endoscope 10. In other words, the coil selecting unit 911 selects the sensing coil 32 having a smallest influence of the marker magnetic field generated by a marker coil 141.

The environmental magnetic field detector 92 takes in the detection signal (reference signal) from the selected sensing coil 32, and acquires the reference value of the magnetic field by applying predetermined processing. Note that processing for the detection signal is similar to that of the first embodiment. In the reference value, marker magnetic field components are smallest and environmental magnetic field components are largest in the sensing coils 32 including non-selected sensing coils 32. That is, an SN ratio is low. Note that an operation of a marker magnetic field detector 55 is similar to that of the first embodiment.

In following step S14, a computing unit 57 corrects the detection values of the magnetic field detected by the sensing coils 32 other than the sensing coil 32 selected in step S13, of the sensing coils 32 of the sensing coil unit 30, using the reference value acquired in step S13. Operations of step S15 and subsequent steps are similar to those of the first embodiment.

As described above, according to the fifth embodiment, it becomes unnecessary to provide a special reference coil unit for acquiring the reference signal. Therefore, the configuration of the position detecting system can be simplified.

Further, according to the fifth embodiment, one sensing coil 32 in the sensing coil unit 30 is used as a reference coil. Therefore, correlation of the environmental magnetic field between the sensing coil 32 selected as the reference coil and the other sensing coils 32 is larger than a case of separately providing a reference coil unit. Therefore, an error of a marker magnetic field component Bm given by the formula (1) can be made small. At this time, the sensing coil 32 most distant from the marker coil 141 is selected as the reference coil, so that the marker magnetic field component included in the reference value is decreased, and a decrease in an SN ratio of the marker magnetic field component Bm provide by the formula (1) can be suppressed.

Note that, in the fifth embodiment, a part or all of the sensing coils 32 may be changed to three-axis coils, similarly to the modification 1-1 (see FIG. 5). In this case, when the three-axis coils (coil set 33) are selected as coils from which the reference signals are to be taken in, the environmental magnetic field detector 92 takes in the detection signals (reference signals) from sensing coils 32X, 32Y, and 32Z included in the coil set 33, and may acquire the reference values of the magnetic field in the X, Y, and Z directions.

Sixth Embodiment

Figure 15:
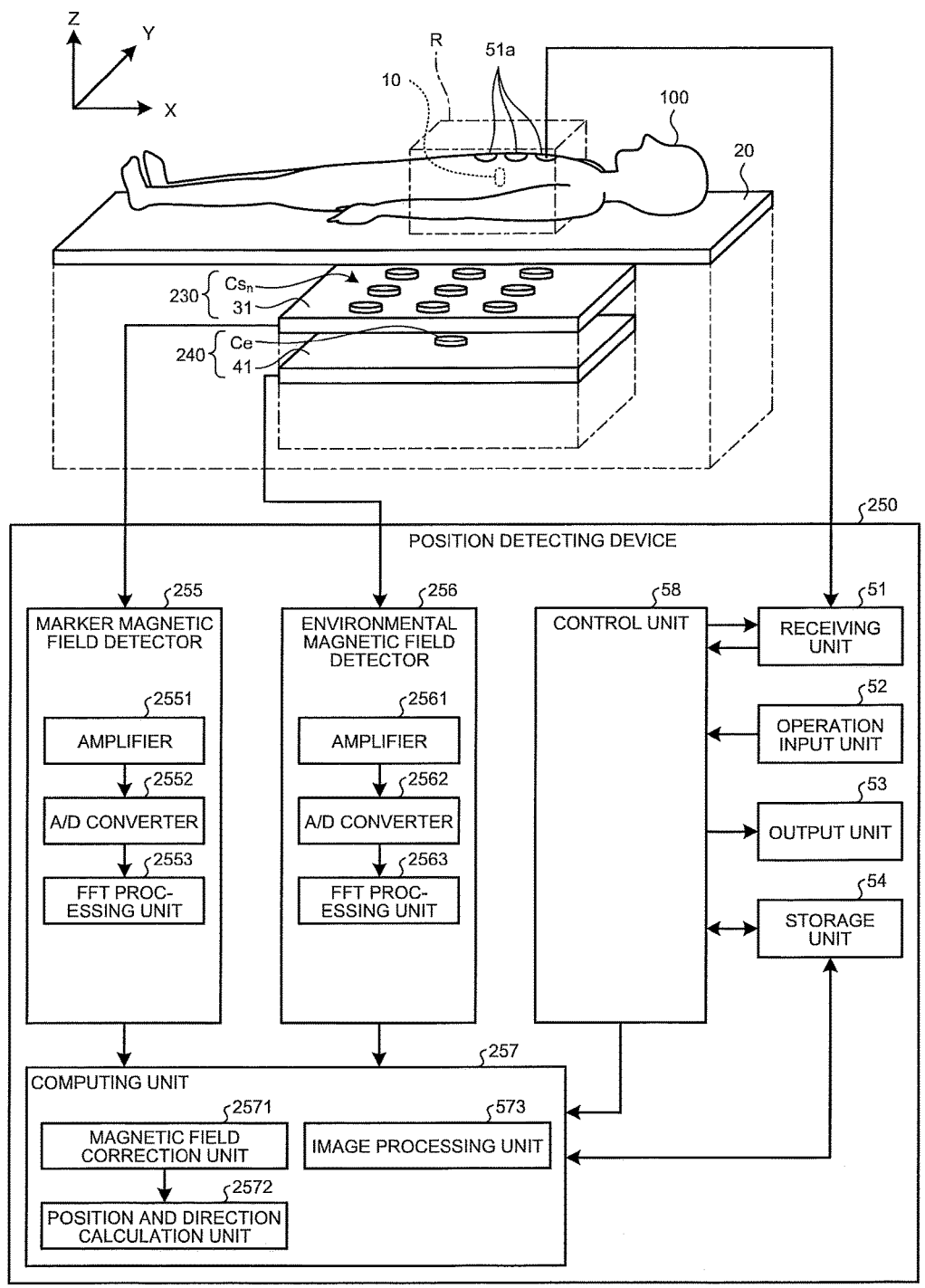
FIG. 15 is a schematic view illustrating a configuration of a position detecting system according to a sixth embodiment of the present invention.

FIG. 15 is a schematic view illustrating a configuration of a position detecting system according to a sixth embodiment of the present invention. As illustrated in FIG. 15, a position detecting system 201 according to the sixth embodiment includes a capsule endoscope 10, a detection coil unit 230 provided under a bed 20 on which a subject 100 is placed, a reference coil unit 240 provided near the detection coil unit 230, and a position detecting device 250 that detects a position of the capsule endoscope 10. In the sixth embodiment, the reference coil unit 240 is arranged under the detection coil unit 230.

Figure 16:
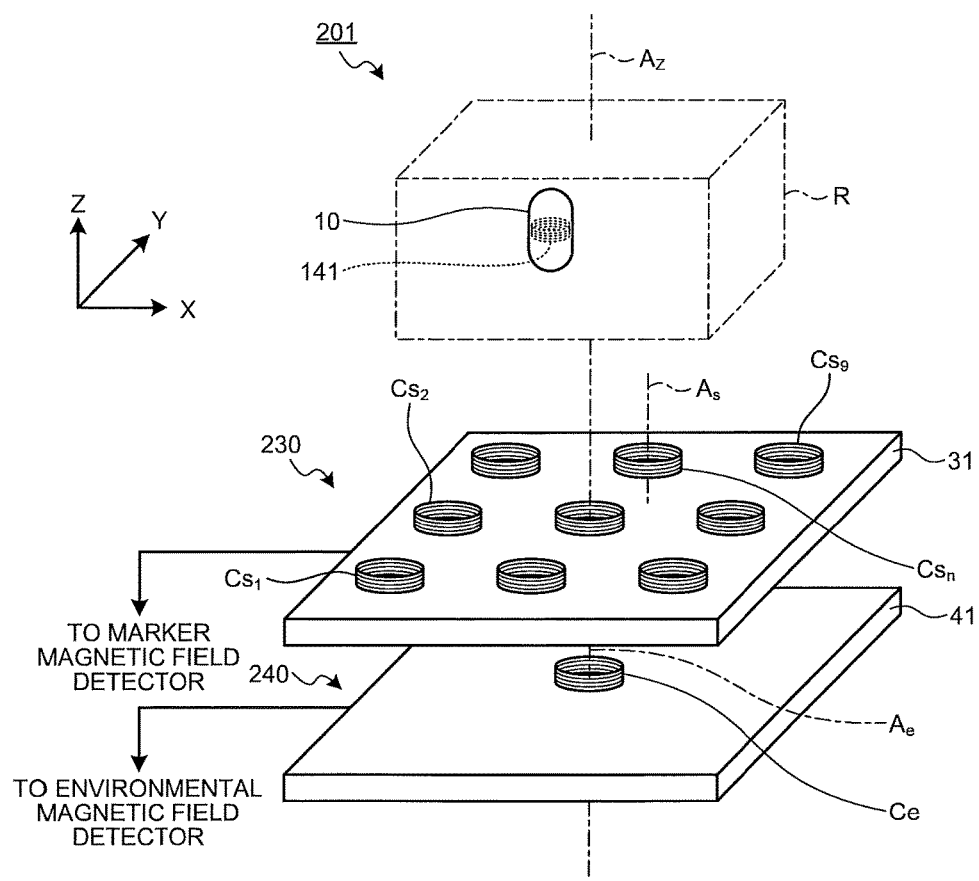
FIG. 16 is an enlarged view of a detection coil unit and a reference coil unit illustrated in FIG. 15.

FIG. 16 is an enlarged view of the detection coil unit 230 and the reference coil unit 240 illustrated in FIG. 15. The detection coil unit 230 and the reference coil unit 240 are arranged such that centers thereof are adjusted to a central axis $A_z$ in a vertical direction of a targeted region R.

The detection coil unit 230 includes a planar panel 31 arranged in parallel to a top surface of the bed 20, and a plurality of detection coils $Cs_n$ (n=1, 2, ..., N; N=9 in FIG. 16) arranged on a principal plane of panel 31. Each of the detection coils $Cs_n$ is, for example, a coil spring tube-shaped coil having sizes of an opening diameter of about 30 to 40 mm and the height of about 5 mm. Each of the detection coils $Cs_n$ receives a marker magnetic field generated by a marker coil (magnetic field generation coil) 141 of the capsule endoscope 10, and outputs a detection signal.

In the panel 31, the plurality of detection coils $Cs_n$ is arranged in a matrix form such that central axes $A_s$ are parallel to a Z direction. In the sixth embodiment, arrangement of the plurality of detection coils $Cs_n$ is not especially limited. However, it is preferable to arranged the detection coils $Cs_n$ to become symmetrical (line-symmetrical or rotation-symmetrical) with respect to a center of the panel 31. Accordingly, the plurality of detection coils $Cs_n$ becomes symmetric to the central axis $A_z$ of the targeted region R.

The reference coil unit 240 includes a planar panel 41 arranged in parallel to the panel 31, and a reference coil Ce arranged on a principal plane of the panel 41. The reference coil Ce is a tube-shaped coil similar to the detection coil $Cs_n$, and detects an environmental magnetic field existing in an installation environment of the position detecting system 201 including a detection space of the marker magnetic field and outputs a detection signal. Hereinafter, the detection signal output by the reference coil Ce is referred to as reference signal. The reference coil Ce is arranged such that a central axis $A_e$ becomes parallel to the Z direction, similarly to the detection coil $Cs_n$.

The reference coil Ce is preferably arranged close to a center of the panel 41 (that is, on an extension of the central axis $A_z$). If the reference coil Ce is arranged in the center of the panel 41, distances between the reference coil Ce and the detection coils $Cs_n$ roughly become uniform, and there are no detection coils $Cs_n$ extremely close to or distant from the reference coil Ce.

Next, positional relationship between the detection coil unit 230 and the reference coil unit 240 will be described. The detection coil unit 230 is arranged near the subject 100 during an examination so that an SN ratio to the maker magnetic field generated by the capsule endoscope 10 becomes high. In the sixth embodiment, the detection coil unit 230 is arranged under the bed 20.

Further, the reference coil unit 240 is preferably arranged as close as possible to the detection coil unit 230 to detect the environmental magnetic field in the positions of the detection coils $Cs_n$. In FIG. 16, the reference coil unit 240 is arranged immediately under the detection coil unit 230. The distance between the panel 31 on which the detection coils $Cs_n$ are arranged and the panel 41 on which the reference coil Ce is arranged is preferably as short as possible.

Referring back to FIG. 15, the position detecting device 250 includes a receiving unit 51, an operation input unit 52, an output unit 53, a storage unit 54, a marker magnetic field detector 255 that applies various types of signal processing to the detection signals output from the detection coils $Cs_n$, an environmental magnetic field detector 256 that applies various types of signal processing to the reference signal output from the reference coil Ce, a computing unit 257, and a control unit 58 that controls operations of respective units.

The marker magnetic field detector 255 includes a plurality of signal processing channels that processes the detection signals output from the detection coils $Cs_n$. Each of the signal processing channel includes am amplifier 2551 that amplifies the detection signal, an A/D converter 2552 that applies A/D conversion processing to the detection signal, and an FFT processing unit 2553 that applies FFT processing to a digital detection signal output from the A/D converter 2552.

The environmental magnetic field detector 256 includes an amplifier 2561 that amplifies the reference signal output from the reference coil Ce, an A/D converter 2562 that performs A/D conversion processing on the reference signal, and an FFT processing unit 2563 that performs FFT processing on a digital reference signal output from the A/D converter 2562.

The computing unit 257 is configured by a CPU and the like, for example, and reads a program stored in the storage unit 54 and performs predetermined calculation processing. To be specific, the computing unit 257 includes a magnetic field correction unit 2571, a position and direction calculation unit 2572, and an image processing unit 573.

The magnetic field correction unit 2571 outputs a value (correction value) of a marker magnetic field component from which an influence of the environmental magnetic field has been removed, by correcting output values of the detection signals output from the signal processing channels of the marker magnetic field detector 255, using the reference signal output from the environmental magnetic field detector 256.

Figure 17:
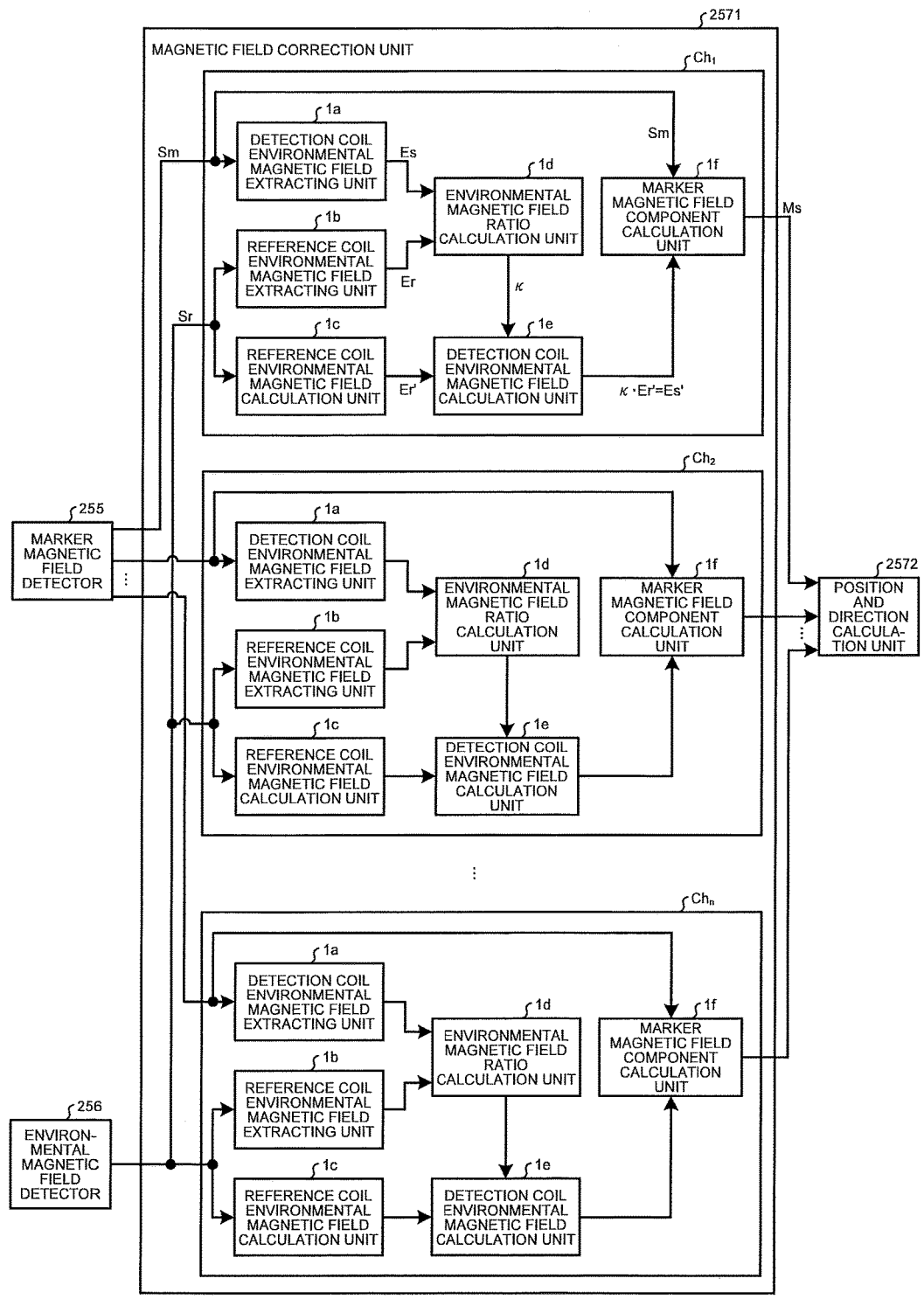
FIG. 17 is a block diagram illustrating a configuration of a magnetic field correction unit illustrated in FIG. 15.

FIG. 17 is a block diagram illustrating a configuration of the magnetic field correction unit 2571. The magnetic field correction unit 2571 includes a plurality of channels $Ch_n$ (n=1, 2, ..., N) corresponding to the detection coils $Cs_n$. Each of the channels $Ch_n$ executes processing of correcting the detection signal, using the reference signal output from the environmental magnetic field detector 256, the detection signal having been output from the detection coil $Cs_n$, and to which predetermined signal processing has been applied in the corresponding signal processing channel of the marker magnetic field detector 255.

To be specific, each of the channels $Ch_n$ includes a detection coil environmental magnetic field extracting unit 1a, a reference coil environmental magnetic field extracting unit 1b, a reference coil environmental magnetic field calculation unit 1c, an environmental magnetic field ratio calculation unit 1d, a detection coil environmental magnetic field calculation unit 1e, and a marker magnetic field component calculation unit 1f.

The detection coil environmental magnetic field extracting unit (first filter) 1a extracts an environmental magnetic field component (first frequency band component) included in a detection signal Sm by applying high-pass (low-range removing) filter processing to the detection signal Sm, and outputs a value (first value) Es of the environmental magnetic field component.

The reference coil environmental magnetic field extracting unit (second filter) 1b extracts an environmental magnetic field component (first frequency band component) included in a reference signal Sr by applying high-pass filter processing to the reference signal Sr, and outputs a value (second value) Er of the environmental magnetic field component.

The reference coil environmental magnetic field calculation unit (third filter) 1c extracts an environmental magnetic field component (second frequency band component) by applying high-pass filter processing of a cut-off frequency different from the reference coil environmental magnetic field extracting unit 1b to the reference signal Sr, and calculates a value (third value) Er' of the environmental magnetic field component.

The environmental magnetic field ratio calculation unit 1d calculates a ratio κ of the value Es of the environmental magnetic field component extracted by the detection coil environmental magnetic field extracting unit 1a, and the value Er of the environmental magnetic field component extracted by the reference coil environmental magnetic field extracting unit 1b.

The detection coil environmental magnetic field calculation unit 1e calculates a value Es' of the environmental magnetic field component included in the detection signal Sm from the ratio κ and the value Er' of the environmental magnetic field component output from the reference coil environmental magnetic field calculation unit 1c.

The marker magnetic field component calculation unit if calculates a value Ms of the marker magnetic field component included in the detection signal Sm by subtracting the value Es' of the environmental magnetic field component from the output value of the detection signal Sm.

Referring back to FIG. 15, the position and direction calculation unit 2572 calculates a position and a direction of the capsule endoscope 10 (inclinations of a long axis La of the capsule endoscope 10 in the X, Y, and Z directions), based on the values Ms of the marker magnetic field component output from the channels $Ch_n$ of the magnetic field correction unit 2571. Hereinafter, information regarding the position and the direction of the capsule endoscope 10 is collectively referred to as positional information.

Figure 18A:
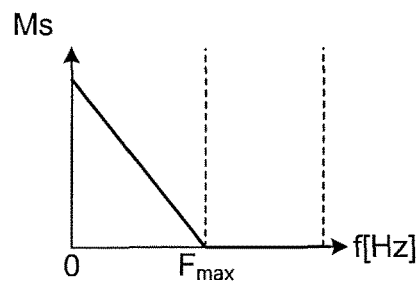
FIGS. 18A to 18C are graphs for explaining a position detecting method in the sixth embodiment of the present invention.
Figure 18B:
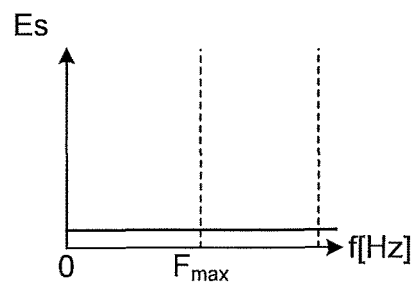
Figure 18C:
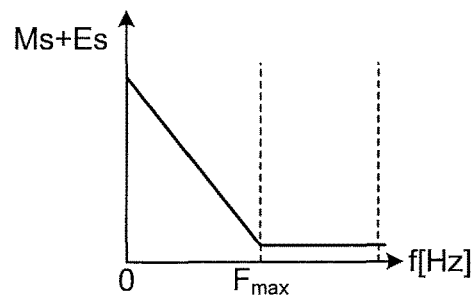
Figure 19A:
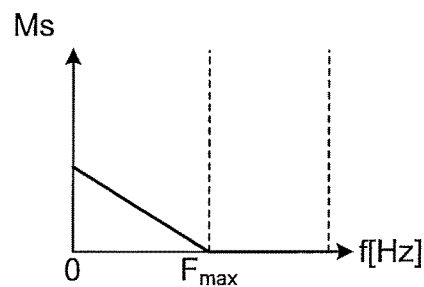
FIGS. 19A to 19C are graphs for explaining a position detecting method in the sixth embodiment of the present invention.
Figure 19B:
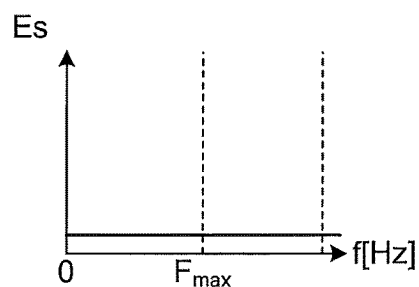
Figure 19C:
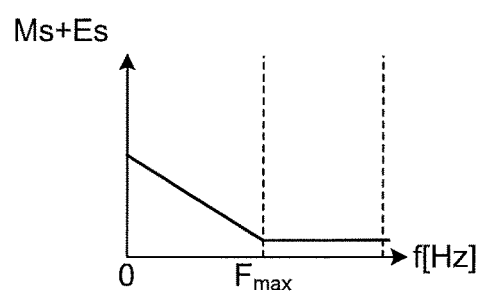
Figure 20A:
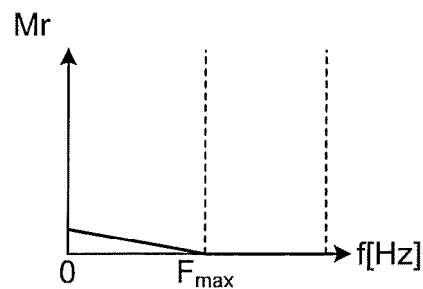
FIGS. 20A to 20C are graphs for explaining a position detecting method in the sixth embodiment of the present invention.
Figure 20B:
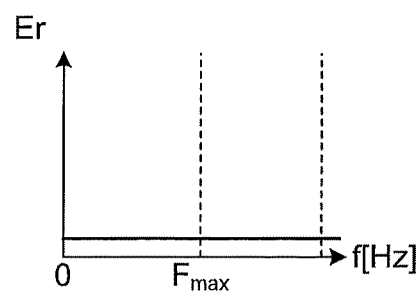
Figure 20C:
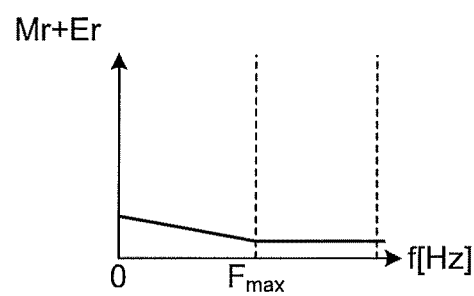

Next, a position detecting method in the sixth embodiment will be described. FIGS. 18A to 20C are graphs for explaining a position detecting method in the sixth embodiment. Among them, FIG. 18A and FIG. 19A illustrate the values Ms of the marker magnetic field components respectively included in the detection signals Sm output from two different detection coils $Cs_n$, FIG. 18B and FIG. 19B illustrate the values Es of the environmental magnetic field components respectively included in the aforementioned detection signals, and FIG. 18C and FIG. 19C illustrate output values of the aforementioned detection signals Sm (sums of the values Ms of the marker magnetic field components and the values Es of the environmental magnetic field components). FIG. 20A illustrates a value Mr of the marker magnetic field component included in the reference signal Sr output from the reference coil Ce, FIG. 20B illustrates the value Er of the environmental magnetic field component included in the aforementioned reference signal, and FIG. 20C illustrates an output value of the reference signal Sr (a sum of the value Mr of the marker magnetic field component and the value Er of the environmental magnetic field component).

Here, in order to perform accurate correction of the detection signals Sm, it is preferable to arrange the reference coil unit 240 as close as possible to the detection coil unit 230, and enhance correlation between the environmental magnetic field in the positions of the detection coils $Cs_n$ and the environmental magnetic field in the position of the reference coil Ce, as illustrated in FIG. 16. However, in this case, as illustrated in FIGS. 20A to 20C, the reference coil Ce detects the marker magnetic field near the detection coils $Cs_n$ in addition to the environmental magnetic field.

As illustrated in FIGS. 18A to 18C and 19A to 19C, the value Ms of the marker magnetic field component included in the detection signal Sm output from the detection coil $Cs_n$ is different depending on the position of the detection coil $Cs_n$. Further, the values Ms of the marker magnetic field components in the detection signals Sm becomes smaller as the frequency becomes higher.

The value Es of the environmental magnetic field component included in the detection signal Sm becomes nearly constant regardless of the position of the detection coil $Cs_n$. Further, the values Es of the environmental magnetic field components in the detection signals Sm become nearly constant regardless of high and low of the frequency.

Such tendencies of the marker magnetic field component and the environmental magnetic field component are similar in the reference signal Sr, as illustrated in FIGS. 20A to 20C. Therefore, in the sixth embodiment, the high-pass filter processing is applied to the detection signals Sm and the reference signal Sr, using the difference between the marker magnetic field and the environmental magnetic field, so that the marker magnetic field component and the environmental magnetic field component are separated. Then, the output values of the detection signals Sm are corrected using the value of the environmental magnetic field component from which the marker magnetic field component included in the reference signal Sr has been removed.

Hereinafter, processing in the channels $Ch_n$ will be described in detail. First, the magnetic field correction unit 2571 sets a maximum frequency $F_{max}$ of the marker magnetic field determined according to the movement of the capsule endoscope 10 to the cut-off frequency in the detection coil environmental magnetic field extracting unit 1a and the reference coil environmental magnetic field extracting unit 1b.

The detection coil environmental magnetic field extracting unit 1a extracts the environmental magnetic field component by applying the high-pass filter processing to the detection signal Sm, using the maximum frequency $F_{max}$ as the cut-off frequency.

Further, the reference coil environmental magnetic field extracting unit 1b extracts the environmental magnetic field component by applying the high-pass filter processing to the reference signal Sr, using the maximum frequency $F_{max}$ as the cut-off frequency.

The environmental magnetic field ratio calculation unit $1d$ then calculates the ratio κ of the value Es of the environmental magnetic field component extracted from the detection signal Sm and the value Er of the environmental magnetic field component extracted from the reference signal Sr. It is preferable to employ a ratio $\sigma_{Es}/\sigma_{Es}$ of a standard deviation $\sigma_{Es}$ of values of high frequency band components extracted from the detection signal Sm and a standard value $\sigma_{Es}$ of values of high-frequency band components extracted from the reference signal Sr as the ratio κ.

Figure 21A:
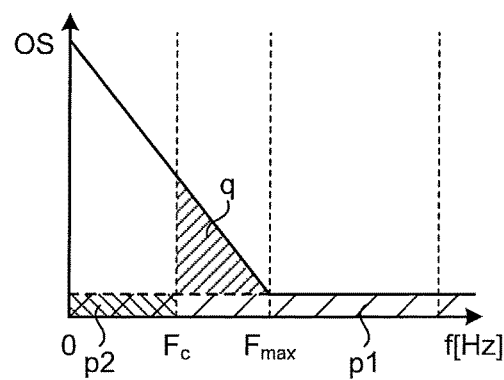
FIGS. 21A to 21C are graphs of strength of a magnetic field detected by a detection coil and a reference coil.
Figure 21B:
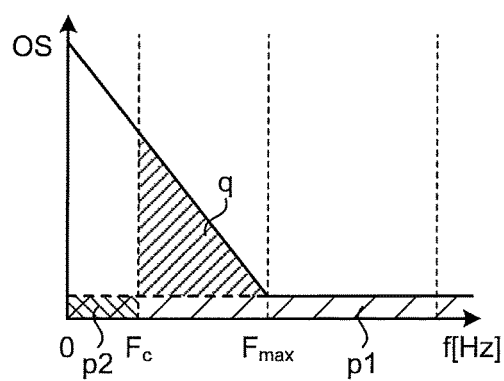
Figure 21C:
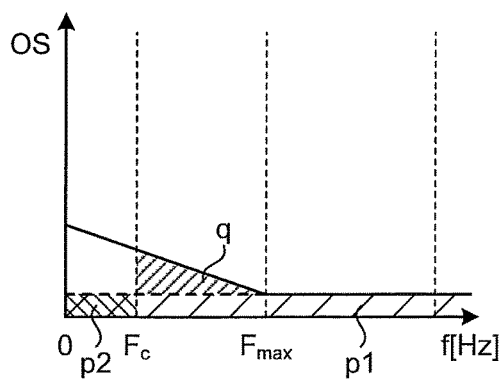

Here, a reason to set the cut-off frequency in the detection coil environmental magnetic field extracting unit $1a$ and the reference coil environmental magnetic field extracting unit $1b$ to the maximum frequency $F_{max}$ will be described with reference to FIGS. 21A to 21C. FIGS. 21A to 21C are graphs illustrating an output value OS of the detection signal Sm or the reference signal Sr output from the detection coil $Cs_n$ or the reference coil Ce.

A case of extracting the environmental magnetic field component by applying the high-pass filter processing to the detection signal Sm or the reference signal Sr of the magnetic field will be considered. If the environmental magnetic field is assumed as white noise, a ratio of the environmental magnetic field component (corresponding to an area of a region p2) cut (decreased) by applying the high-pass filter processing to all of the environmental magnetic field components (corresponding to an area of a region p1) is determined according to a cut-off frequency $F_c$, as illustrated in FIGS. 21A and 21B.

Further, as illustrated in FIGS. 21B and 21C, when the cut-off frequency $F_c$ is the same, a ratio of a decreased component of the environmental magnetic field to all of the environmental magnetic field components is nearly constant regardless of the magnitude of the marker magnetic field. That is, if the cut-off frequency $F_c$ is the same, the ratio of the decreased component of the environmental magnetic field becomes constant between the plurality of detection signals and the reference signal. Therefore, the decreased component of the environmental magnetic field does not influence on the ratio κ of the environmental magnetic field components respectively extracted from the detection signals and the reference signal. Therefore, the maximum frequency $F_{max}$ at which a residual component of the marker magnetic field becomes zero is used as the cut-off frequency $F_c$, so that the ratio κ can be accurately calculated.

Note that, in actually detecting the magnetic field, noise components smaller than the environmental magnetic field, such as noise caused by hardware, are mixed, in addition to the environmental magnetic field. To ignore such small noise components, a standard deviation of values of frequency band components extracted by the filter processing may be used as the value of the environmental magnetic field component.

The maximum frequency $F_{max}$ can be calculated using a maximum moving speed v of the capsule endoscope 10 acquired from a position detection result of the capsule endoscope 10. Here, displacement G (f) of the capsule endoscope 10 using a frequency f of the marker magnetic field as a variable is given by the following formula (3):

$$G(f)=v/(2\pi f)^2 \qquad (3)$$

In the formula (3), the frequency f at which the displacement G becomes sufficiently small is determined as the maximum frequency $F_{max}$. In reality, an upper limit of a permissible positional error is set in advance as a threshold, and the frequency f at which the displacement G becomes the threshold or less may just be obtained.

The magnetic field correction unit 2571 sets a frequency $F_c$ smaller than the maximum frequency $F_{max}$ ($F_c < F_{max}$), as the cut-off frequency in the reference coil environmental magnetic field calculation unit $1c$. The reference coil environmental magnetic field calculation unit $1c$ calculates the value Er' of the environmental magnetic field component by applying the high-pass filter processing to the reference signal Sr at this cut-off frequency $F_c$.

Here, a method of determining the cut-off frequency $F_c$ in calculating the value Er' of the environmental magnetic field component will be described with reference to FIGS. 21A to 21C. In a case of setting the cut-off frequency $F_c$ to the maximum frequency $F_{max}$ or more, the residual component of the marker magnetic field becomes zero. Further, in a case of setting the cut-off frequency Fc to a frequency less than the maximum frequency $F_{max}$, as illustrated in FIG. 21A, the residual component (corresponding to the area of the region q) of the marker magnetic field is increased as the cut-off frequency $F_c$ becomes smaller. As illustrated in FIGS. 21B and 21C, in a case where the cut-off frequency $F_c$ is the same, the residual component (same as the above) of the marker magnetic field is proportional to the strength of the marker magnetic field component.

The decreased component (the area of the region P2) of the environmental magnetic field, which is cut by applying the high-pass filter processing, is increased as the cut-off frequency $F_c$ becomes larger.

In a case of extracting the environmental magnetic field component from the reference signal, an extraction error thereof is equal to a sum of the residual component of the marker magnetic field and the decreased component of the environmental magnetic field. Therefore, the cut-off frequency $F_c$ is determined such that the sum of the residual component of the marker magnetic field and the decreased component of the environmental magnetic field becomes minimum. It is preferable to determine the cut-off frequency $F_c$ to make the strength of the residual component of the marker magnetic field and the strength of the decreased component of the environmental magnetic field become equal. This corresponds to determining the frequency $F_c$ to make the area of the region p2 and the area of the region q become equal, as illustrated in FIG. 21A. Accordingly, the extraction error of the environmental magnetic field component can be decreased. The residual component and the environmental magnetic field component of the marker magnetic field included in the reference signal are temporally changed. Therefore, the cut-off frequency $F_c$ is updated at every timing when the marker magnetic field detector 255 and the environmental magnetic field detector 256 detect the magnetic field.

The detection coil environmental magnetic field calculation unit $1e$ calculates a product of the value Er' of the environmental magnetic field component and the ratio κ calculated as described above, as the value Es' of the environmental magnetic field component in the position of the detection coil $Cs_n$.

Further, the marker magnetic field component calculation unit $1f$ calculates the value Ms of the marker magnetic field component by subtracting the value Es' of the environmental magnetic field component calculated by the detection coil environmental magnetic field calculation unit $1e$ from the output value of the detection signal Sm. The value Ms of the marker magnetic field component is output as the correction value of the detection signal.

Figure 22:
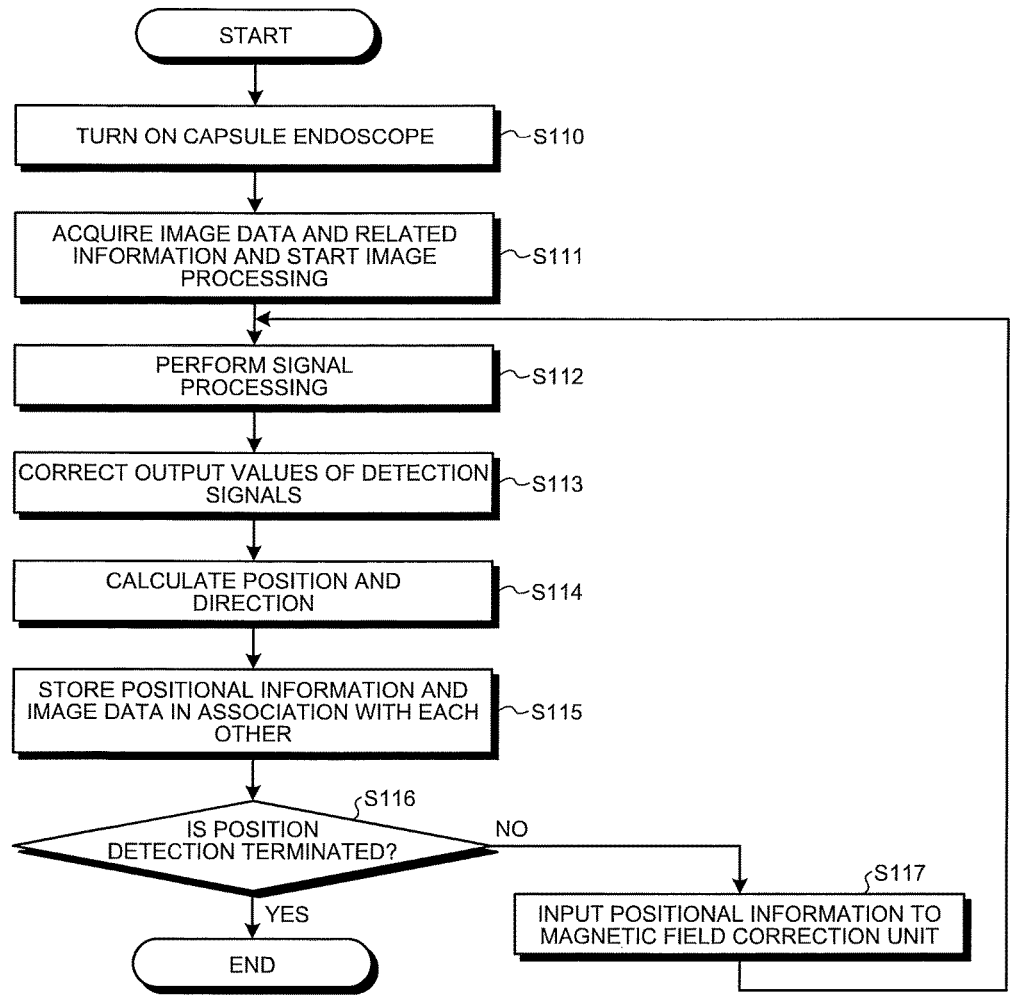
FIG. 22 is a flowchart illustrating an operation of the position detecting system illustrated in FIG. 15.

Next, an operation of the position detecting system 201 will be described with reference to FIG. 22. FIG. 22 is a flowchart illustrating an operation of the position detecting system 201. First, in step S110, the capsule endoscope 10 is turned ON.

In following step S111, the position detecting device 250 receives a radio signal transmitted from the capsule endoscope 10 through a receiving antenna 51a, acquires image data of an in-vivo image superimposed on the radio signal and related information by applying demodulation processing and the like to the radio signal, and starts image processing.

In step S112, the position detecting device 250 acquires the detection signals respectively output from the plurality of detection coils $Cs_n$ and the reference coil Ce output from the reference signal, and applies the predetermined processing such as the amplification processing, the A/D conversion processing, and the FFT processing in the marker magnetic field detector 255 and the environmental magnetic field detector 256.

In step S113, the magnetic field correction unit 2571 acquires the plurality of detection signals from the marker magnetic field detector 255 and the reference signal from the environmental magnetic field detector 256, and corrects the output values of the detection signals using the reference signal. That is, the magnetic field correction unit 2571 calculates the values of the marker magnetic field component, which are obtained by removing the environmental magnetic field component from the detection signals.

Here, the magnetic field correction unit 2571 sets an initial value (fixed value) of the maximum frequency $F_{max}$ as the cut-off frequency of the high-pass filter processing in calculating the ratio κ, when first correcting the output values of the detection signals. Further, in the second and subsequent times, the magnetic field correction unit 2571 acquires a positional change amount per unit time of the capsule endoscope 10 from the position detection result of the previous capsule endoscope 10, calculates the maximum frequency $F_{max}$ using a maximum value of the positional change amount as the maximum moving speed v in the formula (3), and sets the maximum frequency $F_{max}$ as the cut-off frequency.

In step S114, the position and direction calculation unit 2572 calculates the position and the direction of the capsule endoscope 10 based on the correction values output from the channels $Ch_n$ of the magnetic field correction unit 2571.

In step S115, the computing unit 257 stores the position and the direction (positional information) of the capsule endoscope 10 calculated by the position and direction calculation unit 2572 and the image data to which the image processing has been applied by the image processing unit 573 to the storage unit 54 in association with each other.

In step S116, the control unit 58 determines whether terminating the position detection of the capsule endoscope 10. To be specific, the control unit 58 determines that the position detection is to be terminated when the wireless transmission from the capsule endoscope 10 is stopped, or when instruction information of position detection operation termination is input from the operation input unit 52 to the position detecting device 250. Note that the capsule endoscope 10 continues wireless transmission of the image data and generation of the marker magnetic field until the power supply unit 15 is turned OFF or a battery runs out.

When the position detection of the capsule endoscope 10 is not terminated (No in step S116), the position and direction calculation unit 2572 inputs the positional information of the capsule endoscope 10 to the magnetic field correction unit 2571 (step S117). Following that, the operation of the position detecting system 201 returns to step S112. In this case, in following step S113, the maximum frequency $F_{max}$ is calculated based on the positional information of the capsule endoscope 10. When the position detection is terminated (Yes in step S116), the operation of the position detecting system 201 is terminated.

As described above, according to the sixth embodiment of the present invention, the reference coil Ce for detecting the environmental magnetic field is arranged near the detection coils $Cs_n$ for detecting the marker magnetic field generated from the capsule endoscope 10, and the output values of the detection signals output from the detection coils $Cs_n$ are corrected using the reference signal output from the reference coil Ce. Therefore, the environmental magnetic field component that is changed in a short time can be excluded from the output values of the detection signals.

Further, according to the sixth embodiment of the present invention, the environmental magnetic field component included in the detection signal included in the detection signal is calculated in consideration of the correlation (ratio κ) between the environmental magnetic field components respectively extracted from the detection signal and the reference signal, and the output value of the detection signal is corrected using the environmental magnetic field component. Therefore, the correction accuracy can be improved compared with a case of correcting the output value of the detection signal, using the output value of the reference signal as it is. Therefore, by use of such a corrected value, the position and the direction of the capsule endoscope 10 can be accurately detected.

Modification 6-1

Figure 23:
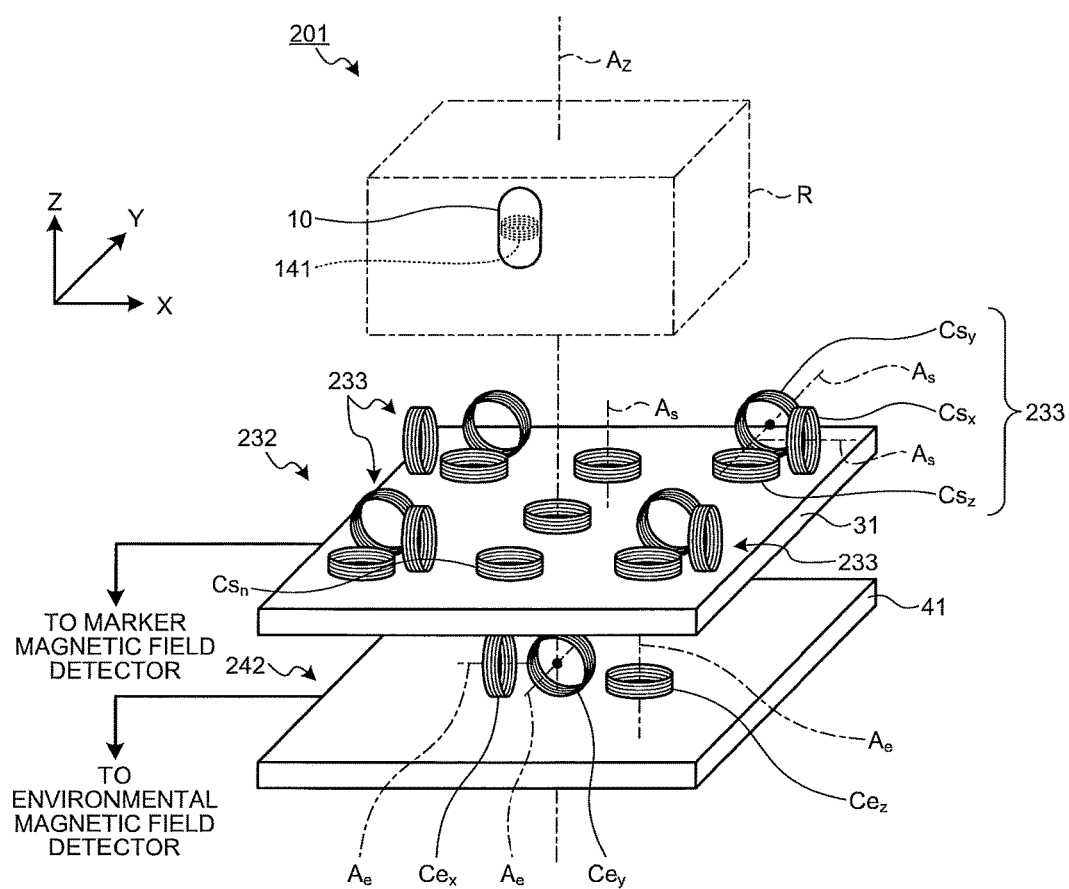
FIG. 23 is a schematic view illustrating a configuration of a position detecting system according to a modification 6-1 of the sixth embodiment of the present invention.

Next, a modification 6-1 of the sixth embodiment of the present invention will be described. FIG. 23 is a schematic view illustrating a configuration of a position detecting system according to a modification 6-1 of the sixth embodiment of the present invention.

In order to enhance position detection accuracy of the capsule endoscope 10, a part or all of detection coils $Cs_n$ illustrated in FIG. 16 may be changed to three-axis coils. For example, in a detection coil unit 232 illustrated in FIG. 23, coils sets 233 that can detect a three-dimensional magnetic field are provided near four corners of a panel 31. Each of the coil sets 233 includes three detection coils $Cs_x$, $Cs_y$, and $Cs_z$ with central axes $A_s$ respectively parallel to an X direction, a Y direction, and a Z direction. Each of the detection coils $Cs_x$, $Cs_y$, and $Cs_z$ detects a magnetic field in the direction of the own central axis $A_s$ and outputs a detection signal. Note that configurations of the detection coils $Cs_x$, $Cs_y$, and $Cs_n$ are similar to those of the detection coils $Cs_n$ illustrated in FIG. 16.

In this case, in a reference coil unit 242 that outputs a reference signal, three reference coils $Ce_x$, $Ce_y$, and $Ce_z$ with central axes $A_e$ parallel to the X direction, the Y direction, and the Z direction are arranged in accordance with the directions of the detection coils $Cs_x$, $Cs_y$, and $Cs_z$. Each of the reference coils $Ce_x$, $Ce_y$, and $Ce_z$ detects a magnetic field in the direction of the own central axis $A_e$ and outputs a reference signal. Note that configurations of the reference coils $Ce_x$, $Ce_y$, and $Ce_z$ are similar to those of the reference coils Ce illustrated in FIG. 16.

The reference coils $Ce_x$, $Ce_y$, and $Ce_z$ are preferably arranged symmetrical (line-symmetrical or point-symmetrical) with respect to a central axis $A_z$ of a targeted region R. In FIG. 23, the reference coils $Ce_x$, $Ce_y$, and $Ce_z$ are arranged on a central line of a panel 41, the central line passing through the central axis A. More preferably, the reference coils $Ce_x$, $Ce_y$, and $Ce_z$ are arranged close to the central axis A. If the reference coils are arranged on the central axis $A_z$, distances between the reference coils $Ce_x$, $Ce_y$, and $Ce_z$ and the detection coils $Cs_n$ become roughly uniform, and there are no detection coils $Cs_n$ that are extremely close to or distant from the reference coils. Therefore, even if local change is caused in the environmental magnetic field, an influence thereof can be suppressed.

When the coil sets 233 are arranged as described above, in correcting the output values of the detection signals in step S113 of FIG. 22, calculation is performed using the reference signals output from the reference coils $Ce_x$, $Ce_y$, and $Ce_z$ facing the same directions as the detection coils $Cs_x$, $Cs_y$, and $Cs_z$. That is, correction is performed using the reference signal output from the reference coil $Ce_x$ for the detection signal output from the detection coil $Cs_x$. The same applies to the detection coils $Cs_y$ and $Cs_z$. Accordingly, correction according to the directions of the environmental magnetic field can be performed.

Modification 6-2

Next, a modification 6-2 of the sixth embodiment of the present invention will be described. In the sixth embodiment, the plurality of channel $Ch_n$ is provided in the magnetic field correction unit 2571, and the plurality of detection signals respectively output from the plurality of detection coils $Cs_n$ is processed in parallel in these channels $Ch_n$. However, the plurality of detection signals may be sequentially processed. In this case, a memory that temporarily stores a plurality of detection signals output from a marker magnetic field detector 255 is provided, and the detection signals are sequentially read from the memory. Environmental magnetic field component extraction processing, ratio κ calculation processing, environmental magnetic field component calculation processing using the ratio κ, and marker magnetic field component calculation processing of subtracting the environmental magnetic field component from the output values of the detection signals are executed using the reference signals output from the environmental magnetic field detector 256, and the output values are sequentially output to the position and direction calculation unit 2572.

Seventh Embodiment

Figure 24:
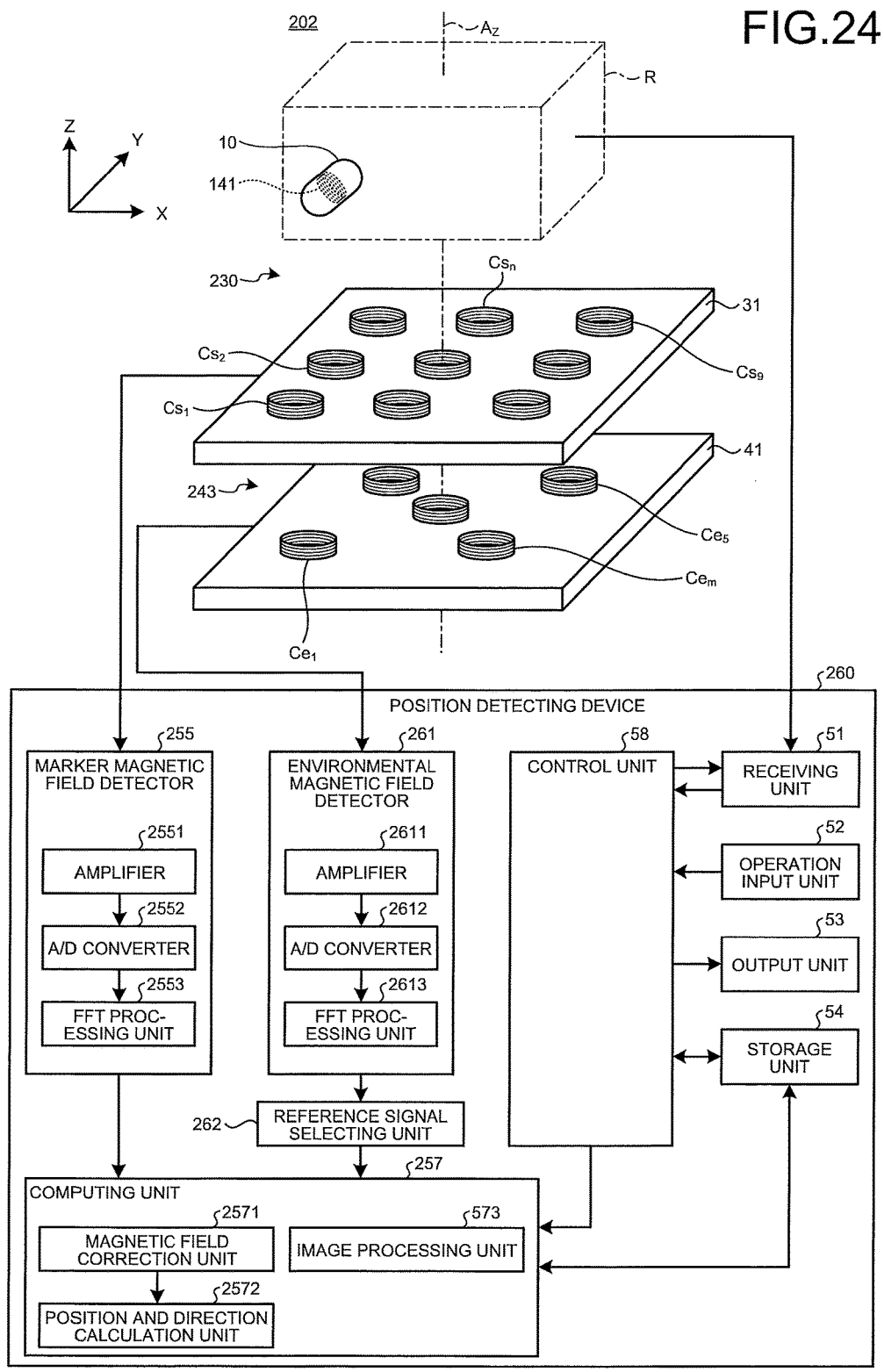
FIG. 24 is a schematic view illustrating a configuration of a position detecting system according to a seventh embodiment of the present invention.

Next, a seventh embodiment of the present invention will be described. FIG. 24 is a schematic view illustrating a configuration of a position detecting system according to a seventh embodiment of the present invention. As illustrated in FIG. 24, a position detecting system 202 according to the seventh embodiment includes a capsule endoscope 10, a detection coil unit 230, a reference coil unit 243, and a position detecting device 260. Among them, configurations and operations of the capsule endoscope 10 and the detection coil unit 230 are similar to those of the sixth embodiment.

The reference coil unit 243 includes a panel 41, and a plurality of reference coils $Ce_m$ (m=1, 2, ... M; M=5 in FIG. 24) arranged on the panel 41. Configurations and a direction of arrangement of the reference coils $Ce_m$ are similar to those of the reference coils Ce illustrated in FIG. 16. Such a reference coil unit 243 is arranged in parallel to the detection coil unit 230 near the detection coil unit 230.

The position detecting device 260 includes an environmental magnetic field detector 261 in place of an environmental magnetic field detector 256 illustrated in FIG. 15, and further includes a reference signal selecting unit 262. Configurations and operations of respective units of the position detecting device 260 except the environmental magnetic field detector 261 and the reference signal selecting unit 262 are similar to those of the sixth embodiment.

The environmental magnetic field detector 261 includes a plurality of signal processing channels that processes reference signals output from the plurality of reference coils $Ce_m$. Each of the signal processing channels includes am amplifier 2611 that amplifies the reference signal, an A/D converter 2612 that applies A/D conversion processing to the detection signal, and an FFT processing unit 2613 that applies FFT processing to a digital detection signal output from the A/D converter 2612.

The reference signal selecting unit 262 selects one reference signal to be used in a magnetic field correction unit 2571, from among the plurality of signal processing channels of the environmental magnetic field detector 261, and inputs the reference signal to the channels $Ch_n$ (see FIG. 17) of the magnetic field correction unit 2571. To be specific, the reference signal selecting unit 262 selects the reference signal having the smallest marker magnetic field component, of the plurality of reference signals output from the environmental magnetic field detector 261, as the reference signal to be used in the magnetic field correction unit 2571. Here, as illustrated in FIGS. 18A to 20C, a value of the environmental magnetic field component is nearly constant regardless of a level of the entire signal, and the marker magnetic field components included in the reference signal are smaller as the level of the reference signal is smaller. Therefore, an influence of the marker magnetic field components included in the reference signal on the correction of the detection signal can be decreased.

Figure 25:
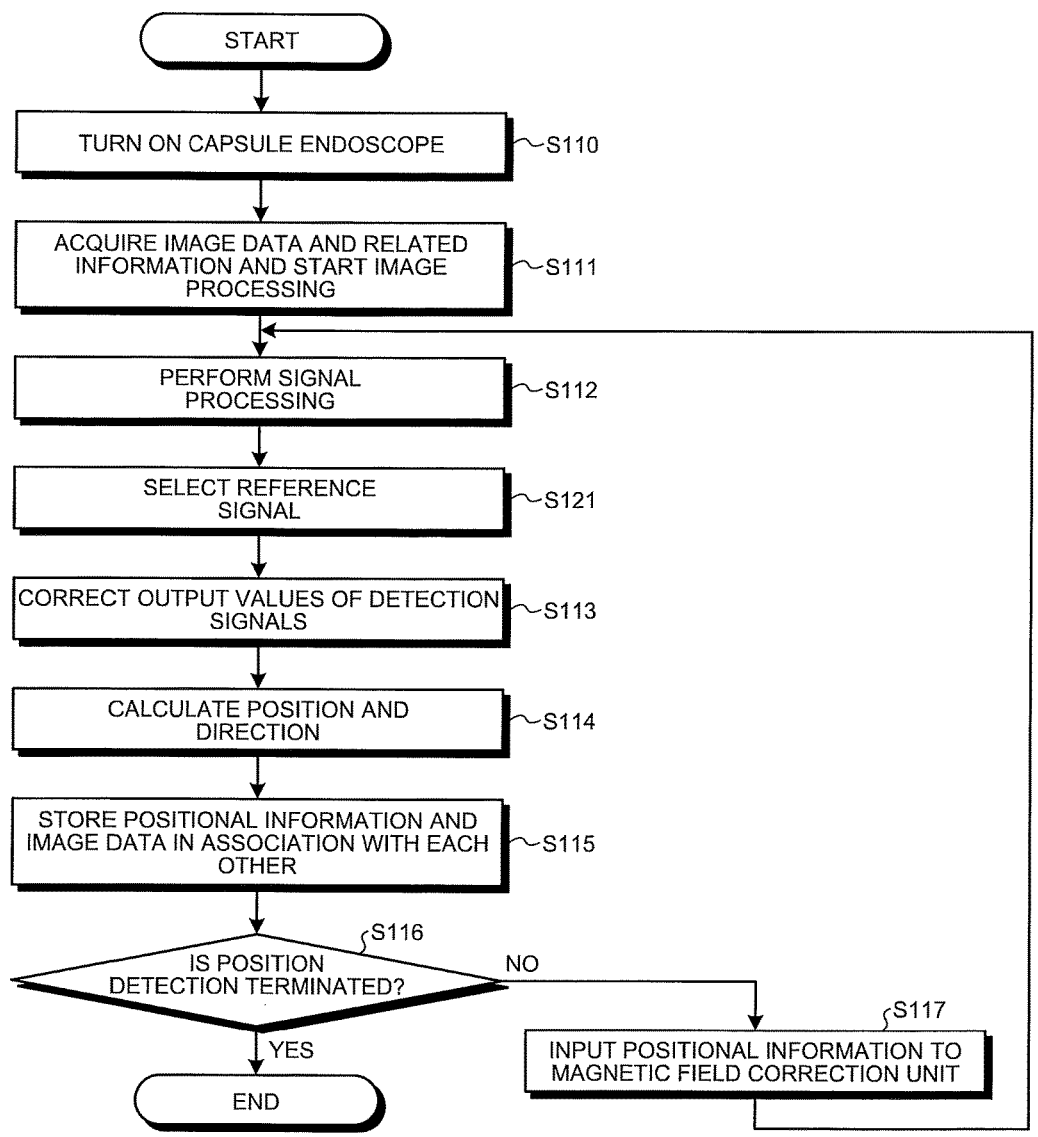
FIG. 25 is a flowchart illustrating an operation of the position detecting system illustrated in FIG. 24.

Next, an operation of the position detecting system 202 will be described. FIG. 25 is a flowchart illustrating an operation of the position detecting system 202. In the flowchart, steps S110 to S112 are similar to those of the sixth embodiment (see FIG. 22).

In step S121 following step S112, the reference signal selecting unit 262 selects the reference signal having the smallest signal level, based on signal levels of the reference signals respectively output from the plurality of signal processing channels of the environmental magnetic field detector 261, and outputs the reference signal to the channels $Ch_n$ of the magnetic field correction unit 2571. Operations of step S113 following step S121 and subsequent steps are similar to those of the sixth embodiment.

As described above, according to the seventh embodiment of the present invention, the reference signal having a small influence of the marker magnetic field component is selected and used from the reference signals output from the plurality of reference coils $Ce_m$. Therefore, correction of the detection signals can be more accurately performed.

Modification 7

Figure 26:
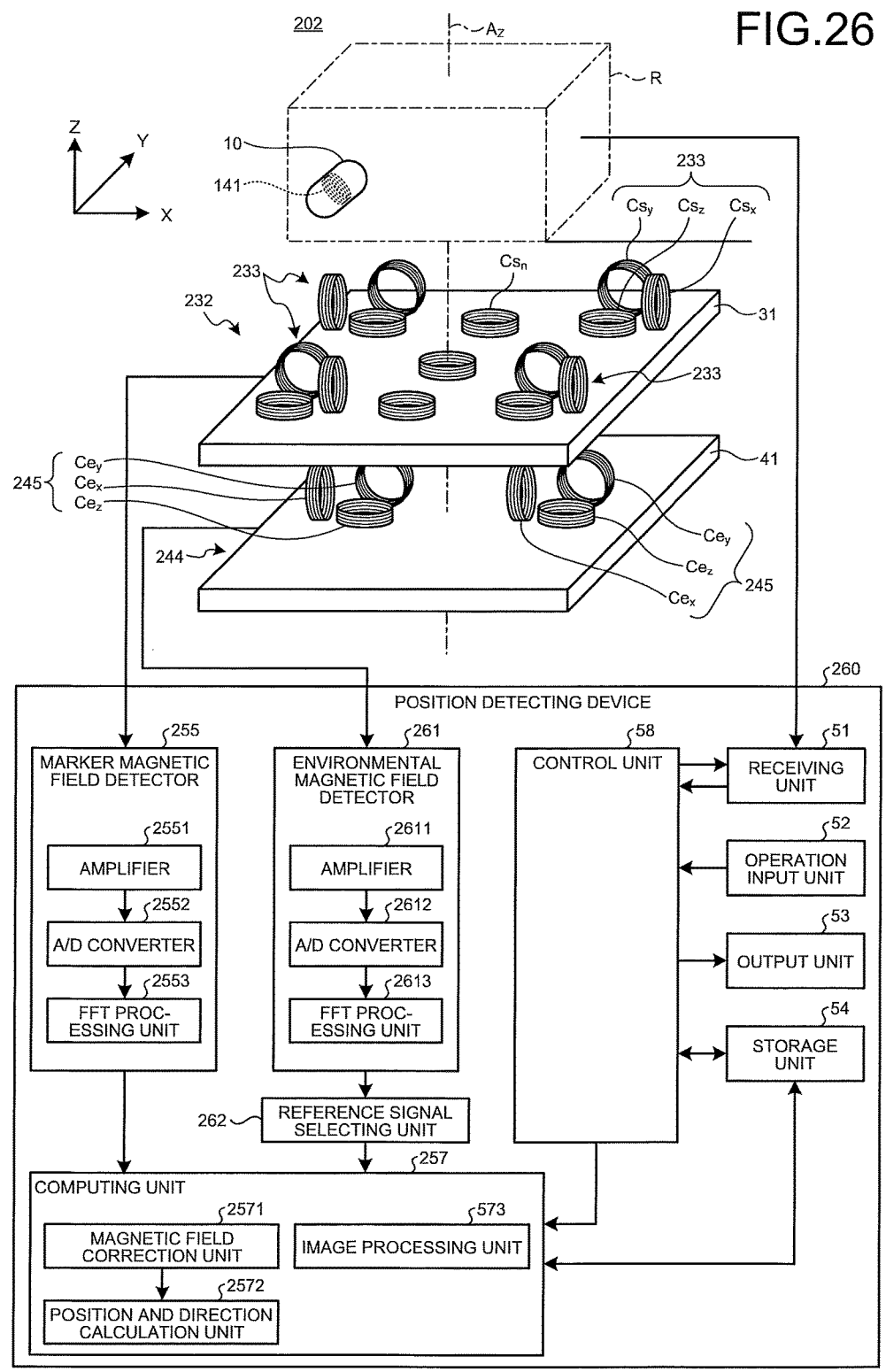
FIG. 26 is a schematic view illustrating a configuration of a position detecting system according to a modification 7 of the seventh embodiment of the present invention.

Next, a modification 7 of the seventh embodiment of the present invention will be described. FIG. 26 is a schematic view illustrating a configuration of a position detecting system according to the modification 7 of the seventh embodiment of the present invention.

In a case of providing three-axis coils (coil sets 233) in a detection coil unit 232, like the modification 6-1 of the sixth embodiment, a plurality of three-axis coils may be provided at a reference coil unit side. In a reference coil unit 244 illustrated in FIG. 26, two sets of coil sets 245 made of three reference coils $Ce_x$, $Ce_y$, and $Ce_z$ are provided on a panel 41.

In this case, in correcting output values of detection signals in step S113 of FIG. 25, calculation is performed using a reference signal having a small signal level among reference signals output from reference coils $Ce_x$, $Ce_y$, and $Ce_z$ respectively facing the same directions as detection coils $Cs_x$, $Cs_y$, and $Cs_z$. That is, correction for the detection signal output from the detection coil $Cs_x$ is performed using the reference signal having a smaller signal level, of the reference signals respectively output from the two reference coils $Ce_x$. The same applies to the detection coils $Cs_y$ and $Cs_z$. Accordingly, correction according to the direction of the environmental magnetic field can be performed.

Eighth Embodiment

Figure 27:
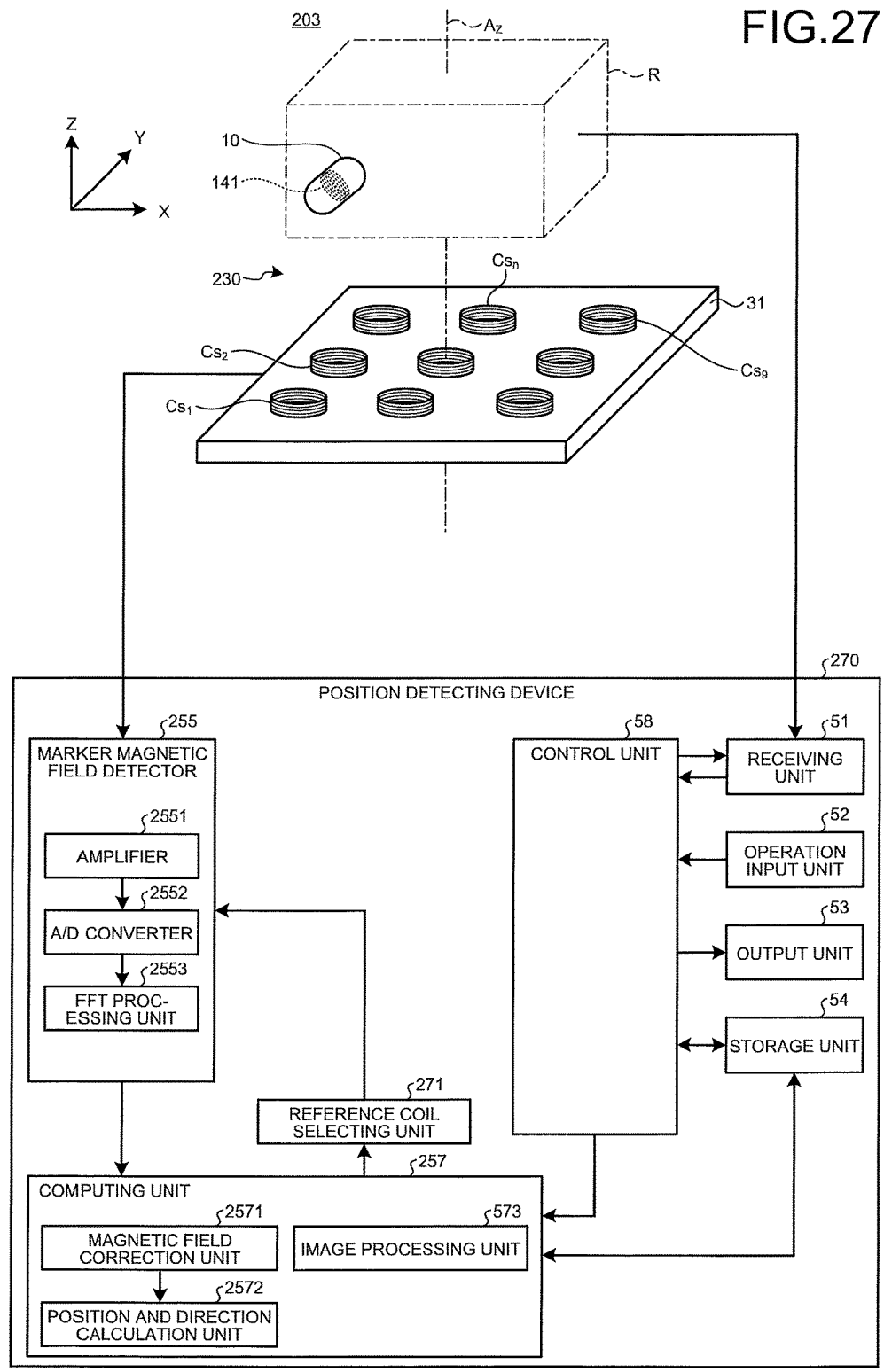
FIG. 27 is a schematic view illustrating a configuration of a position detecting system according to an eighth embodiment of the present invention.

Next, an eighth embodiment of the present invention will be described. FIG. 27 is a schematic view illustrating a configuration of a position detecting system according to an eighth embodiment of the present invention. As illustrated in FIG. 27, a position detecting system 203 according to the eighth embodiment of the present invention includes a capsule endoscope 10, a detection coil unit 230, and a position detecting device 270. Configurations and operations of the capsule endoscope 10 and the detection coil unit 230 are similar to those of the sixth embodiment.

The position detecting device 270 includes a reference coil selecting unit 271, in place of an environmental magnetic field detector 256 in a position detecting device 250 illustrated in FIG. 15. The reference coil selecting unit 271 selects a magnetic field detection coil $Cn_s$ to be used as a reference coil, from among a plurality of magnetic field detection coils $Cn_s$, based on correction results of the detection signals by a magnetic field correction unit 2571. Configurations and operations of respective units of the position detecting device 270 except the reference coil selecting unit 271 are similar to those of the sixth embodiment.

Figure 28:
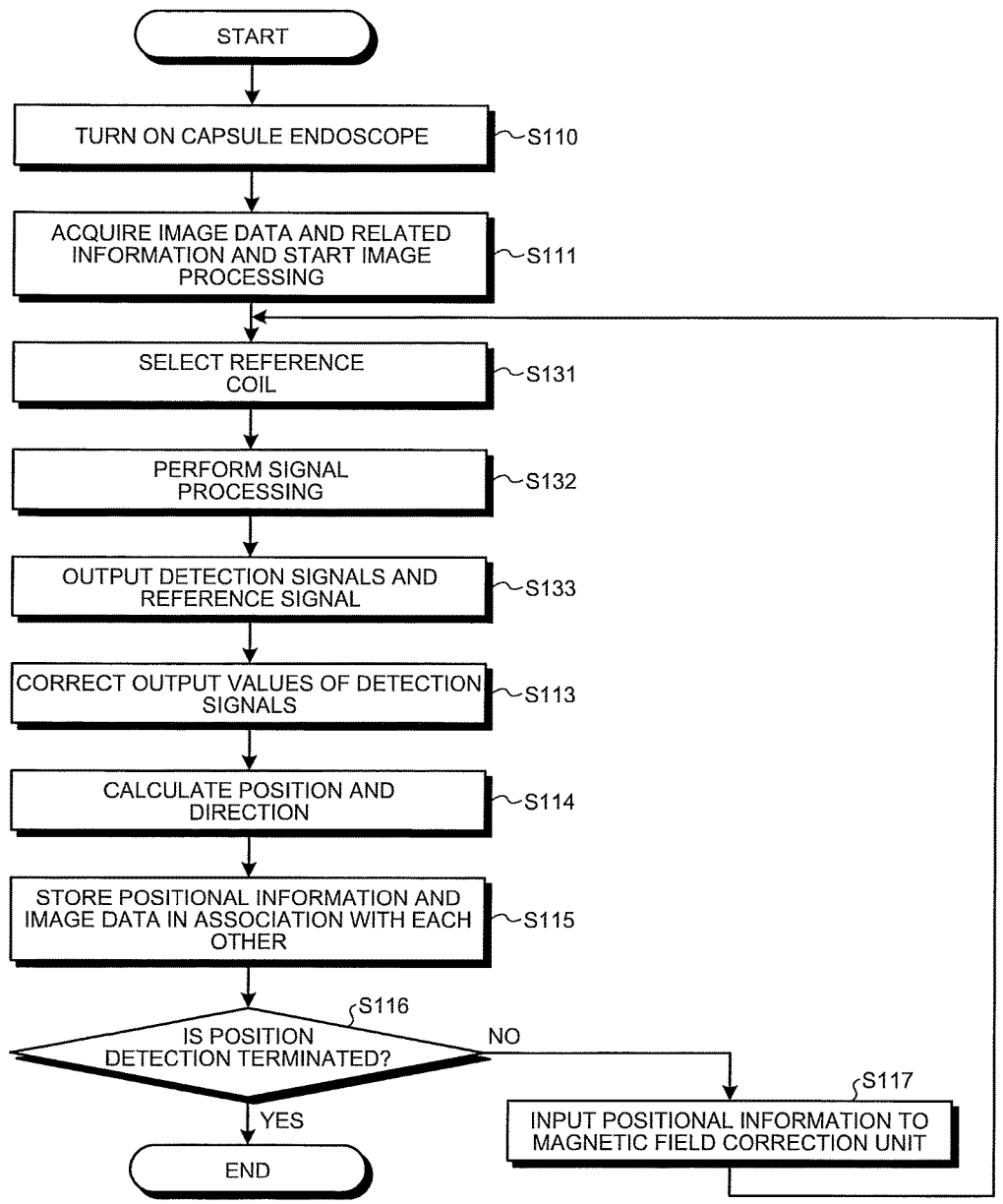
FIG. 28 is a flowchart illustrating an operation of the position detecting system illustrated in FIG. 27.

Next, an operation of the position detecting system 203 will be described. FIG. 28 is a flowchart illustrating an operation of the position detecting system 203. In the flowchart, steps S110 and S111 are similar to those of the sixth embodiment (see FIG. 22).

In step S131 following step S111, the reference coil selecting unit 271 acquires the correction results of the detection signals from the magnetic field correction unit 2571, and selects the detection coil $Cs_n$ that outputs the detection signal having the smallest marker magnetic field component, as the reference coil. Note that, in a case where position detection of the capsule endoscope 10 has not yet been performed (that is, at the time of an operation of the first time), the reference coil selecting unit 271 selects the detection coil $Cs_n$ determined in advance.

In following step S132, the marker magnetic field detector 255 acquires the detection signals output from the detection coils $Cs_n$, and applies predetermined processing such as amplification processing, A/D conversion processing, and FFT processing.

In following step S133, the marker magnetic field detector 255 outputs the detection signal of the detection coil $Cs_n$ selected by the reference coil selecting unit 271 to channels of the magnetic field correction unit 2571 as the reference signal, and outputs the detection signals of the other detection coils $Cs_n$ to corresponding channels $Ch_n$. Operations of following steps S113 to S117 are similar to those of the sixth embodiment. After step S117, the operation of the position detecting system 203 returns to step S131.

As described above, according to the eighth embodiment of the present invention, one of the plurality of detection coils is used as the reference coil. Therefore, correlation of environmental magnetic field components between the detection signals and the reference signal becomes high, and the environmental magnetic field components included in the detection signal can be more accurately removed.

Ninth Embodiment

Figure 29:
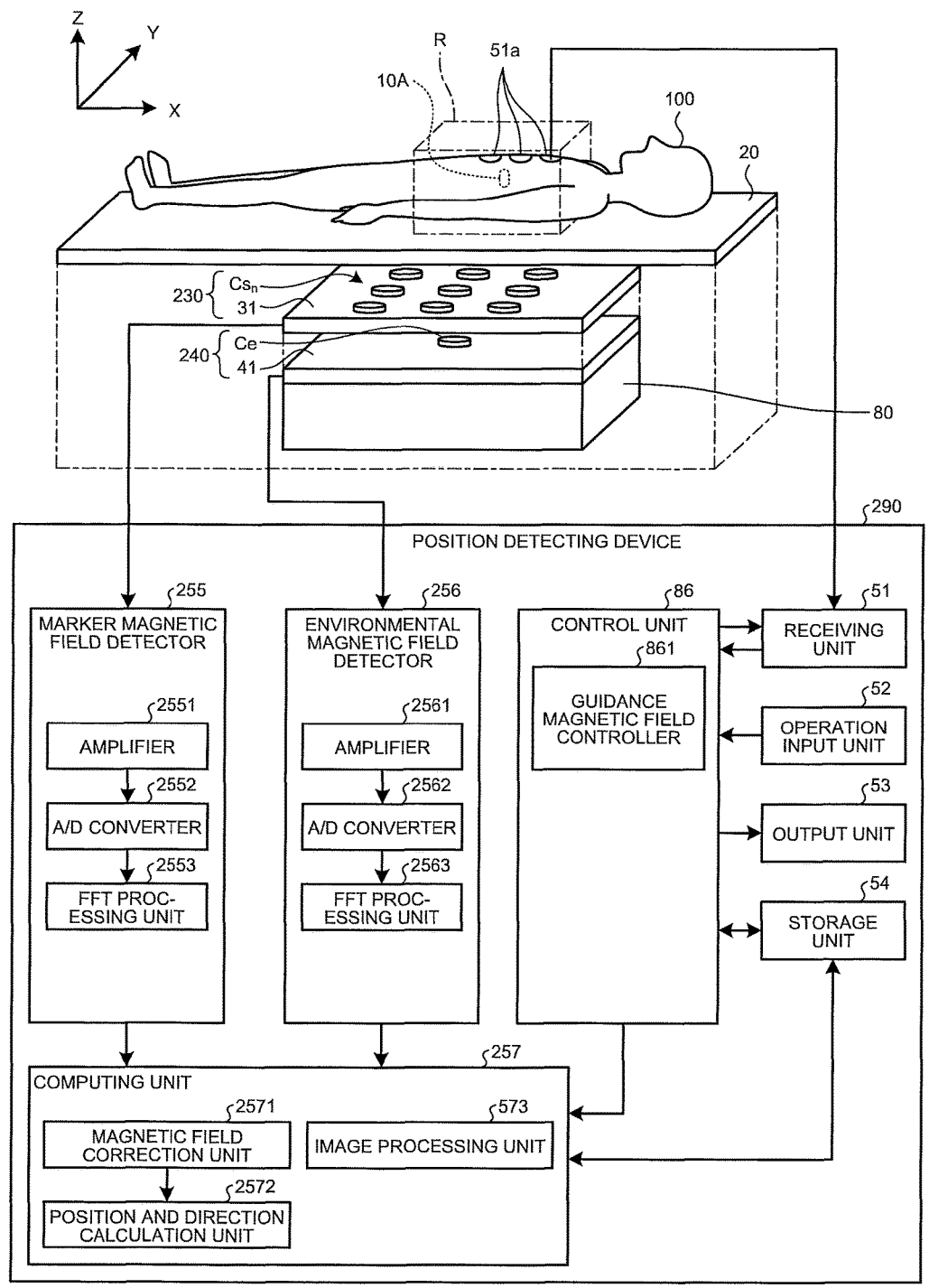
FIG. 29 is a schematic view illustrating a configuration of a position detecting system according to a ninth embodiment of the present invention.

Next, a ninth embodiment of the present invention will be described. FIG. 29 is a schematic view illustrating a configuration of a position detecting system according to the ninth embodiment of the present invention. As illustrated in FIG. 29, a position detecting system 204 according to the ninth embodiment includes a capsule endoscope 10A, a detection coil unit 230, a reference coil unit 240, a guidance magnetic field generation unit 80 that generates a guidance magnetic field for guiding the capsule endoscope 10A, and a position detecting device 290. Among them, configurations and operations of the detection coil unit 230 and the reference coil unit 240 are similar to those of the sixth embodiment. Further, a configuration of the guidance magnetic field generation unit 80 is similar to that of the modification 4-4 of the fourth embodiment.

In the ninth embodiment, in a case of generating the guidance magnetic field and guiding the capsule endoscope 10A, a magnetic field correction unit 2571 sets a cut-off frequency (maximum frequency $F_{max}$) in high-pass filter processing in calculating a ratio κ of environmental magnetic field components respectively included in a detection signal and a reference signal, based on control information output by a guidance magnetic field controller 861. That is, a frequency f at which displacement G (f) of the capsule endoscope 10A given by the formula (3), using a speed v of the capsule endoscope 10A guided under control of the guidance magnetic field controller 861 becomes a threshold or less is determined as the maximum frequency $F_{max}$.

Note that, in the ninth embodiment, a detection coil unit 232 provided with three-axis coils and a reference coil unit 242 (see FIG. 23) or a reference coil unit 244 (see FIG. 26) may be applied in place of the detection coil unit 230 and the reference coil unit 240, or a reference coil unit 243 provided with a plurality of reference coils $Ce_m$ (see FIG. 24) may be applied in place of the reference coil unit 240. Alternatively, similarly to the eighth embodiment, one of a plurality of detection coils $Cs_n$ may be used as the reference coil.

According to some embodiments, a position of a capsule medical device can be accurately detected, excluding an influence of an environmental magnetic field that is changed in a short time.

The first to ninth embodiments and modifications thereof described above are merely examples for implementing the present invention, and the present invention is not limited by these embodiments and modifications. Further, the present invention can generate various inventions by appropriately combining the plurality of configuration elements disclosed in the first to ninth embodiments and the modifications. The present invention can be changed in various manners according to a specification and the like, other various embodiments being able to be made within the scope of the present invention is obvious from the above description.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A position detecting system comprising:
a capsule medical device having therein a magnetic field generation coil for generating a magnetic field;
a plurality of detection coils configured to detect the magnetic field generated by the magnetic field generation coil, and to output a plurality of detection signals;
at least one reference coil configured to detect a magnetic field and to output a detection signal, and arranged at a position where a signal-to-noise ratio to the magnetic field generated by the magnetic field generation coil is smaller than a signal-to-noise ratio in each of the detection signals detected by the plurality of detection coils; and
a magnetic field correction unit configured to correct a plurality of magnetic field detection values based on the plurality of detection signals respectively output from the plurality of detection coils, using at least one reference magnetic field detection value that is a detection value of the magnetic field based on the detection signal output from the at least one reference coil.

2. The position detecting system according to claim 1, wherein
the plurality of detection coils is arranged on a first plane,
the at least one reference coil is arranged on a second plane parallel to the first plane, and
a distance between the first plane and the second plane is larger than a distance between the first plane and a targeted region for detecting the capsule medical device.

3. The position detecting system according to claim 2, wherein
the second plane is located at one side of the first plane, and the targeted region is located at the other side of the first plane.

4. The position detecting system according to claim 1, further comprising:
a storage unit configured to store the plurality of magnetic field detection values and the at least one reference magnetic field detection value; and
a correction factor calculation unit configured to:
calculate a ratio between a magnetic field detection value based on a first detection signal output from at least one of the plurality of detection coils when the magnetic field generation coil does not generate the magnetic field, and a reference magnetic field detection value based on a second detection signal output from the at least one reference coil at same timing as the first detection signal; and
store the ratio in the storage unit, wherein the magnetic field correction unit is configured to:
calculate a correction value in accordance with the ratio and a reference magnetic field detection value based on a third detection signal output from the at least one reference coil when the magnetic field generation coil generates the magnetic field; and
correct the plurality of magnetic field detection values based on the plurality of detection signals respectively output from the plurality of detection coils at same timing as the third detection signal, using the correction value.

5. The position detecting system according to claim 4, wherein
the plurality of detection coils includes three detection coils whose central axes are oriented at different directions,
the at least one reference coil includes three reference coils whose central axes are oriented at different directions, and
the correction factor calculation unit is configured to calculate the ratio between the magnetic field detection value based on the first detection signal output from a detection coil of the three detection coils, and the reference magnetic field detection value based on the second detection signal output from a reference coil of the three reference coils, a central axis of the detection coil being parallel to a central axis of the reference coil.

6. The position detecting system according to claim 1, further comprising:
a position calculation unit configured to calculate a position of the capsule medical device, based on the plurality of magnetic field detection values;
one or more additional reference coils; and
a control unit configured to select one reference coil from among the at least one reference coil and the one or more additional reference coils, based on a result of position calculation of the capsule medical device by the position calculation unit, wherein
the magnetic field correction unit is configured to correct the plurality of magnetic field detection values, using the reference magnetic field detection value based on the detection signal output from the one reference coil selected by the control unit.

7. The position detecting system according to claim 1, wherein
the magnetic field correction unit is configured to perform, on each of the detection signals output from the plurality of detection coils:
first filter processing for outputting a first value of a first frequency band component included in the detection signals;
second filter processing for outputting a second value of the first frequency band component included in the detection signal output from the at least one reference coil;
third filter processing for outputting a third value of a second frequency band component different from the first frequency band component included in the detection signal output from the at least one reference coil;
ratio calculation processing for calculating a ratio between the first value and the second value;
environmental magnetic field calculation processing for calculating a value of an environmental magnetic field component included in the detection signals output from the plurality of detection coils, using the ratio and the third value; and
subtraction processing for calculating a value of a magnetic field component of the magnetic field generated by the magnetic field generation coil, by subtracting the value of the environmental magnetic field component from output values of the detection signals output from the plurality of detection coils.

8. The position detecting system according to claim 7, further comprising:
one or more additional reference coils; and
a reference signal selecting unit configured to select a reference signal to be used by the magnetic field correction unit, from among detection signals respectively output from the at least one reference coil and the one or more additional reference coils, wherein the magnetic field correction unit is configured to correct the plurality of magnetic field detection values, using the reference signal selected by the reference signal selecting unit.

9. The position detecting system according to claim 7, wherein
the magnetic field correction unit is configured to set a maximum frequency of the magnetic field generated by the magnetic field generation coil, as a cut-off frequency in the first filter processing and second filter processing.

10. The position detecting system according to claim 9, further comprising a position calculation unit configured to calculate a position of the capsule medical device, based on the plurality of magnetic field detection values, wherein
the magnetic field correction unit is configured to determine the cut-off frequency in the first filter processing and the second filter processing, based on a result of calculation by the position calculation unit.

11. The position detecting system according to claim 9, wherein
the capsule medical device comprises a permanent magnet, and
the position detecting system further comprises:
a guidance magnetic field generation unit provided outside the capsule medical device and configured to generate a guidance magnetic field for guiding the capsule medical device by applying the guidance magnetic field to the permanent magnet; and
a guidance magnetic field controller configured to output control information for controlling an operation of the guidance magnetic field generation unit, wherein
the magnetic field correction unit is configured to determine the cut-off frequency in the first filter processing and the second filter processing, based on the control information.

12. A position detecting system comprising:
a capsule medical device having therein a magnetic field generation coil for generating a magnetic field;
a plurality of detection coils, each of which is configured to detect the magnetic field generated by the magnetic field generation coil, and to output a detection signal;
a control unit configured to select at least one detection coil from among the plurality of detection coils; and
a magnetic field correction unit configured to correct a plurality of magnetic field detection values based on a plurality of detection signals respectively output from detection coils that are not selected by the control unit from among the plurality of detection coils, using a reference magnetic field detection value that is a detection value of the magnetic field based on the detection signal output from the at least one detection coil selected by the control unit.

13. The position detecting system according to claim 12, further comprising a position calculation unit configured to calculate a position of the capsule medical device, based on the plurality of magnetic field detection values, wherein
the control unit is configured to select one of the plurality of detection coils having a smallest signal-to-noise ratio to the magnetic field generated by the magnetic field generation coil, based on a result of position calculation of the capsule medical device by the position calculation unit.

14. The position detecting system according to claim 12, wherein
the magnetic field correction unit is configured to perform, on each of detection signals output from the plurality of detection coils:
first filter processing for outputting a first value of a first frequency band component included in the detection signals;
second filter processing for outputting a second value of the first frequency band component included in the detection signal output from the at least one detection coil selected by the control unit;
third filter processing for outputting a third value of a second frequency band component different from the first frequency band component included in the detection signal output from the at least one detection coil selected by the control unit;
ratio calculation processing for calculating a ratio between the first value and the second value;
environmental magnetic field calculation processing for calculating a value of an environmental magnetic field component included in the detection signals output from the plurality of detection coils, using the ratio and the third value; and
subtraction processing for calculating a value of a magnetic field component of the magnetic field generated by the magnetic field generation coil, by subtracting the value of the environmental magnetic field component from output values of the detection signals output from the plurality of detection coils.

15. The position detecting system according to claim 14, wherein
the magnetic field correction unit is configured to set a maximum frequency of the magnetic field generated by the magnetic field generation coil, as a cut-off frequency in the first filter processing and the second filter processing.

* * * * *